(12) United States Patent
Porter et al.

(10) Patent No.: US 10,539,489 B2
(45) Date of Patent: Jan. 21, 2020

(54) METHODS FOR ACQUIRING PLANAR VIEW STEM IMAGES OF DEVICE STRUCTURES

(71) Applicant: Micron Technology, Inc., Boise, ID (US)

(72) Inventors: Jamie C. Porter, Kuna, ID (US); Scott M. Williams, Boise, ID (US); Clint R. Davlin, Nampa, ID (US); Joel B. LeBret, Meridian, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 16/526,704

(22) Filed: Jul. 30, 2019

(65) Prior Publication Data

US 2019/0353566 A1 Nov. 21, 2019

Related U.S. Application Data

(63) Continuation of application No. 16/135,821, filed on Sep. 19, 2018, now Pat. No. 10,401,265, which is a continuation-in-part of application No. 15/984,581, filed on May 21, 2018, now Pat. No. 10,410,829.

(60) Provisional application No. 62/650,529, filed on Mar. 30, 2018.

(51) Int. Cl.
| G01N 1/32 | (2006.01) |
| H01J 37/20 | (2006.01) |
| H01J 37/28 | (2006.01) |
| H01J 37/30 | (2006.01) |
| H01J 37/305 | (2006.01) |

(52) U.S. Cl.
CPC ............... G01N 1/32 (2013.01); H01J 37/20 (2013.01); H01J 37/28 (2013.01); H01J 37/3002 (2013.01); H01J 37/3056 (2013.01)

(58) Field of Classification Search
USPC ........................................................ 250/307
See application file for complete search history.

(56) References Cited

U.S. PATENT DOCUMENTS

| 5,435,850 | A | 7/1995 | Rasmussen | |
| 5,851,413 | A | 12/1998 | Casella et al. | |
| 8,884,247 | B2 | 11/2014 | Miller et al. | |
| 9,576,772 | B1 * | 2/2017 | Arjavac | H01J 37/28 |
| 2014/0061032 | A1 * | 3/2014 | Miller | G01N 1/32 |
| | | | | 204/192.33 |
| 2014/0217283 | A1 | 8/2014 | Blackwood et al. | |
| 2015/0075972 | A1 | 3/2015 | Senowitz | |

(Continued)

*Primary Examiner* — Kiet T Nguyen
(74) *Attorney, Agent, or Firm* — TraskBritt

(57) ABSTRACT

A method of preparing a sample that includes milling an initial deep lamella within a wafer using a focused ion beam. The initial deep lamella includes at least one internal structure within an upper portion of the initial deep lamella. The method further includes lifting the initial deep lamella out of the wafer, placing the initial deep lamella on an upper surface of the wafer on a lateral side of the initial lamella, milling a planar shallow lamella out of a portion of the initial deep lamella and the wafer beneath the initial deep lamella to include at least substantially an entire length of the at least one internal structure of the initial deep lamella, lifting the planar shallow lamella out of the wafer, and placing the planar shallow lamella on a carbon grid.

20 Claims, 22 Drawing Sheets

(56) References Cited

U.S. PATENT DOCUMENTS

2015/0369710 A1 12/2015 Fuller et al.
2017/0250055 A1 8/2017 Keady et al.

* cited by examiner

METHODS FOR ACQUIRING PLANAR VIEW STEM IMAGES OF DEVICE STRUCTURES

CROSS-REFERENCE TO RELATED APPLICATIONS

This application is a continuation of U.S. patent application Ser. No. 16/135,821, filed Sep. 19, 2018, pending, which application is a continuation-in-part of U.S. patent application Ser. No. 15/984,581, filed May 21, 2018, which application claims the benefit under 35 U.S.C. § 119(e) of U.S. Provisional Patent Application Ser. No. 62/650,529, filed Mar. 30, 2018, the disclosures of each of which are hereby incorporated herein in their entirety by this reference.

TECHNICAL FIELD

This disclosure relates generally to methods of making lamellae, to transmission electron microscope imaging ("TEM"), and to scanning transmission electron microscope ("STEM") imaging. More specifically, this disclosure relates to methods for acquiring a planar TEM or STEM image of internal structures of a device such as a semiconductor device or a microelectromechanical system (MEMS) device.

BACKGROUND

Thin samples are conventionally cut (e.g., milled) from bulk sample material when determining a quality of microstructures formed on or in a semiconductor or other material. The samples are typically less than about 100 nm thick. Some techniques of forming lamellae are referred to as "lift-out" techniques. These techniques use focused ion beams to cut the sample (e.g., lamella) from a substrate or bulk sample. Such techniques can be useful in analyzing the results of processes used in the fabrication of integrated circuits. Some techniques extract a sample sufficiently thin for use directly in a transmission electron microscope; other techniques extract a "chunk" or larger sample that requires additional thinning before observation. In addition, these "lift-out" specimens may also be directly analyzed by other analytical tools, other than TEM.

BRIEF DESCRIPTION OF THE DRAWINGS

For a detailed understanding of the present disclosure, reference should be made to the following detailed description, taken in conjunction with the accompanying drawings, in which like elements have generally been designated with like numerals, and wherein.

DETAILED DESCRIPTION

Figure 1:
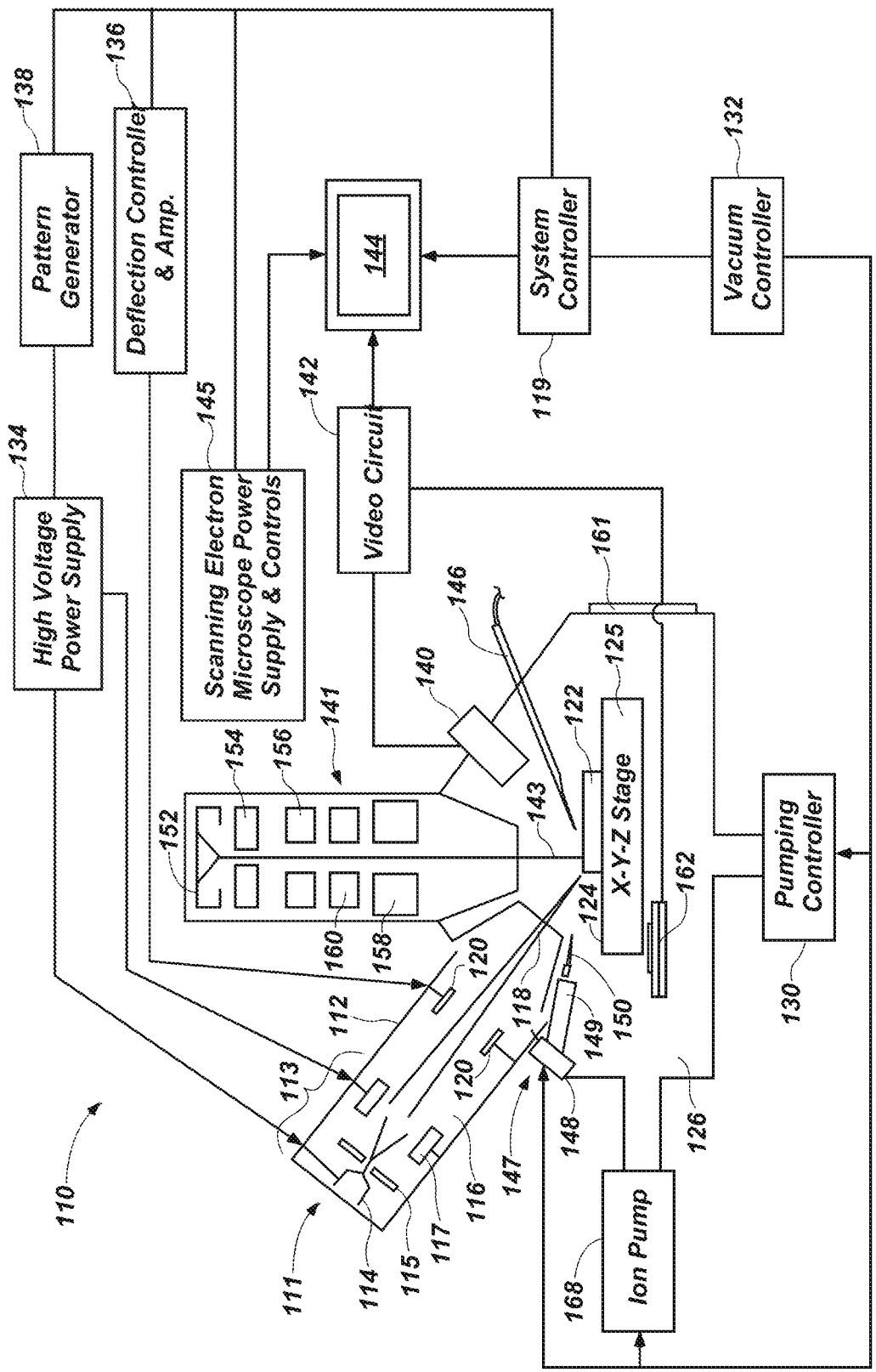
FIG. 1 is a schematic depiction of a dual beam system suitable for performing methods according to one or more embodiments of the present disclosure.

The illustrations presented herein are not actual views of any dual beam system, lamella, or any component thereof, but are merely idealized representations, which are employed to describe embodiments of the present invention.

As used herein, the singular forms following "a," "an," and "the" are intended to include the plural forms as well, unless the context clearly indicates otherwise.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, any relational term, such as "first," "second," "top," "bottom," "upper," "lower," etc., is used for clarity and convenience in understanding the disclosure and accompanying drawings, and does not connote or depend on any specific preference or order, except where the context clearly indicates otherwise. For example, these terms may refer to orientations of elements of a dual beam system, wafer, and/or lamella in conventional orientations. Furthermore, these terms may refer to orientations of elements of a dual beam system, wafer, and/or lamella as illustrated in the drawings.

As used herein, the term "substantially" in reference to a given parameter, property, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

As used herein, the phrases "a planar STEM image," "a planar TEM image," "a planar STEM view," and "a planar TEM view," and any derivative phrases may refer to a view of internal structures of a semiconductor device (e.g., a wafer) or of MEMS structures of a substrate that depicts the internal structures as if viewed from a plane parallel to an upper surface of the semiconductor device.

As used herein, the terms "wafer" and "substrate" mean and include materials upon which and in which structures including feature dimensions of micrometer and nanometer are partially or completely fabricated. Such terms include conventional semiconductor (e.g., silicon) wafers, as well as bulk substrates of semiconductor and other materials. Such structures may include, for example, integrated circuitry (active and passive), MEMS devices, and combinations thereof.

Semiconductor manufacturing, including the fabrication of integrated circuits, may include the use of photolithography, among other processes. A semiconductor substrate (e.g., a silicon wafer) on which circuits are being formed is typically coated with a material, such as a photoresist, that changes solubility when exposed to radiation. A lithography tool, such as a mask or reticle, is typically positioned between a radiation source and the semiconductor substrate and casts a shadow to control that areas of the substrate that are exposed to radiation from the radiation source. After the exposure to the radiation, the photoresist is removed from either the exposed or the unexposed areas of the wafer, leaving a patterned layer of photoresist on the wafer that may protect portions of the wafer surface during any subsequent etching or diffusion processes while selectively exposing other portions for treatment. Similar techniques are employed in the fabrication of MEMS devices.

The photolithography process allows multiple integrated circuit devices, referred to as "dice" or "chips," or MEMS devices, to be formed on each wafer or other substrate. The wafer is often then cut up, or "singulated," into individual segments, each segment including a single integrated circuit device (i.e., die) or MEMS device. Ultimately, these structures are conventionally subjected to additional operations and packaged.

During the manufacturing process, variations in exposure and focus require that the patterns developed by lithographic processes be continually monitored or measured to determine if the dimensions and locations of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing, also termed "pitch," of interconnecting metallization lines, spacing and diameter of contact holes and vias, and the surface geometry such as corners and edges of various features. As features on the wafer are three-dimensional structures, a complete characterization should describe not just a surface dimension, such as the top width of a line or trench, but a complete three-dimensional profile of the feature. Process engineers must be able to accurately measure various critical dimensions ("CD") of such surface features to fine tune the fabrication process and to assure a desired device geometry.

Conventionally, CD measurements are made using instruments such as a scanning electron microscope ("SEM"). In a SEM, a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

In a scanning transmission electron microscope (STEM), a primary electron beam is focused to a fine spot, and the spot is scanned across the sample surface. Electrons that are transmitted through the substrate are collected by an electron detector on the far side of the sample, and the intensity of each point on the image corresponds to the number of electrons collected as the primary beam impacts a corresponding point on the surface.

Transmission electron microscopes (TEMs) allow observers to see extremely small features, on the order of nanometers. In contrast to SEMs, which only image the surface of a material, TEMs allows the additional capability to analyze the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Accordingly, samples are typically less than 100 nm thick.

As semiconductor geometries continue to shrink, manufacturers increasingly rely on TEMs for monitoring the process, analyzing defects, and investigating interface layer morphology. The term "TEM" as used herein refers to a TEM or a STEM, and references to preparing a sample for a TEM are to be understood to also include preparing a sample for viewing on an STEM. Because a sample must be very thin for viewing with transmission electron microscopy (whether TEM or STEM), preparation of a usable sample can be delicate, time-consuming work.

Thin TEM samples cut from a bulk sample material are known as "lamellae." Lamellae are typically less than 100 nm thick, but for some applications a lamella must be considerably thinner. With advanced semiconductor fabrication processes at 30 nm and below, a lamella may need to be less than 20 nm in thickness in order to avoid overlap among small scale structures.

Some techniques of forming lamellae are referred to as "lift-out" techniques. These techniques use focused ion beams in a vacuum chamber to cut the sample (e.g., lamella) from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples. Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the focused ion beam ("FIB") system vacuum chamber are commonly referred to as "in-situ" techniques; sample removal outside the vacuum chamber (as when the entire wafer is transferred to another tool for sample removal) are call "ex-situ" techniques.

Some embodiments of the present disclosure include a process of preparing a sample of semiconductor material (e.g., a wafer) having integrated circuitry formed over an active surface thereof to provide a planar STEM and/or TEM image of the internal structures of the semiconductor material. The process may include loading a wafer into the dual beam system to create (e.g., ion mill) an initial lamella (referred to hereinafter as the "initial lamella") from the wafer. For instance, the dual beam system may mill the initial lamella via any of the methods known in the art. In addition, the process may include creating a nest near a milling site of the initial lamella. The nest may be sized and shaped to receive an upper portion (i.e., a rectangular portion) of the initial lamella. In some embodiments, the nest may include a carbon material. The process may further include lifting and placing the initial lamella on an upper surface of the wafer with a probe. For instance, the process may include lifting and placing the initial lamella with a lamella extraction station. In one or more embodiments, the initial lamella may be disposed flat on the upper surface of the wafer. The process may include placing the initial lamella on the upper surface of the wafer at a location proximate to the nest and then sliding the initial lamella along the upper surface of the wafer into the nest. The process may further include milling a second lamella (referred to hereinafter as the "planar lamella") to include at least a portion of an upper portion of the initial lamella. Additionally, the process may include lifting the planar lamella from the second milling site and placing the planar lamella on an amorphous carbon grid for imaging with a TEM and/or STEM.

In view of the foregoing, because the initial lamella is milled, placed on its side on the upper surface of the wafer, milled again as a portion of the planar lamella, and then placed on the amorphous grid, when the planar lamella and, specifically, the portion of the planar lamella including the upper portion of the initial lamella is imaged, a planar cross-section view of the initial lamella is achieved that is not achievable utilizing conventional operations of the dual beam system. For instance, the planar lamella includes a first cross-sectional view of internal structures of the wafer within the portion of the planar lamella not comprising the initial lamella, and a second cross-sectional view of the internal structures that is orthogonal to the first cross-sectional view within the portion of the planar lamella comprising the initial lamella. The first cross-sectional view may include a view depicting internal structures as if viewed from a plane orthogonal to the upper surface of the wafer, and the second cross-section view may include a view depicting internal structures as if viewed from a plane parallel to the upper surface of the wafer. Typically, at best, conventional methods only achieve the first cross-sectional view.

Figure 2A:
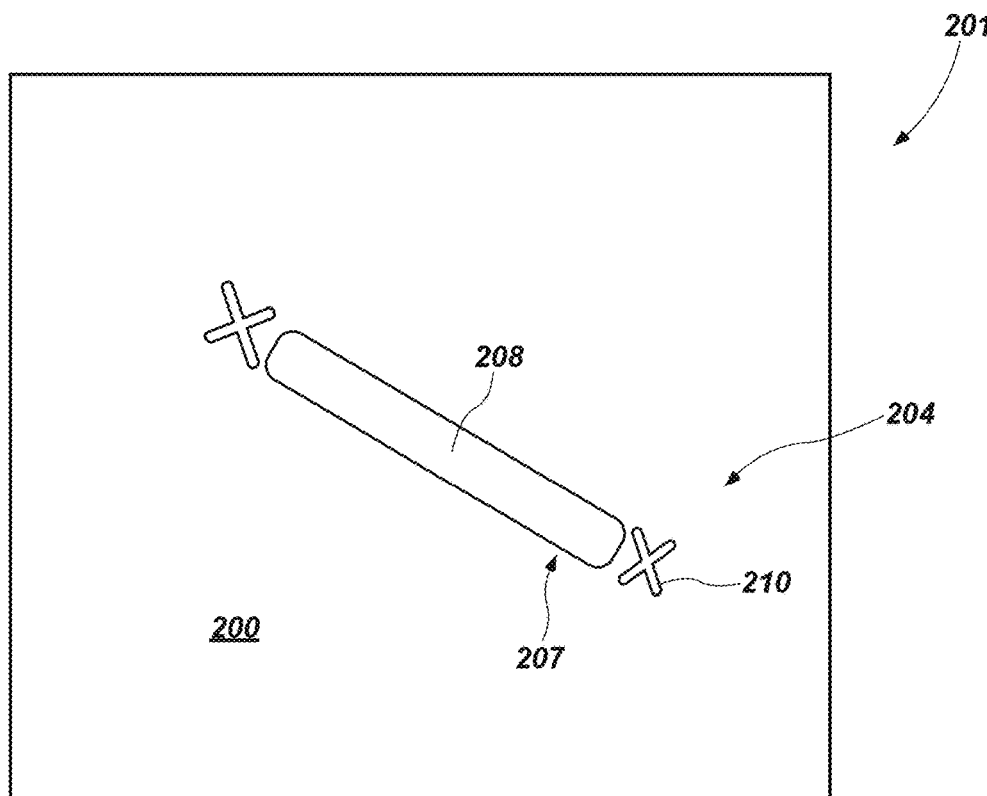
FIGS. 2A-2N illustrate acts of a process for preparing a sample of a semiconductor device for TEM and/or STEM imaging according to one or more embodiments of the present disclosure.
Figure 2B:
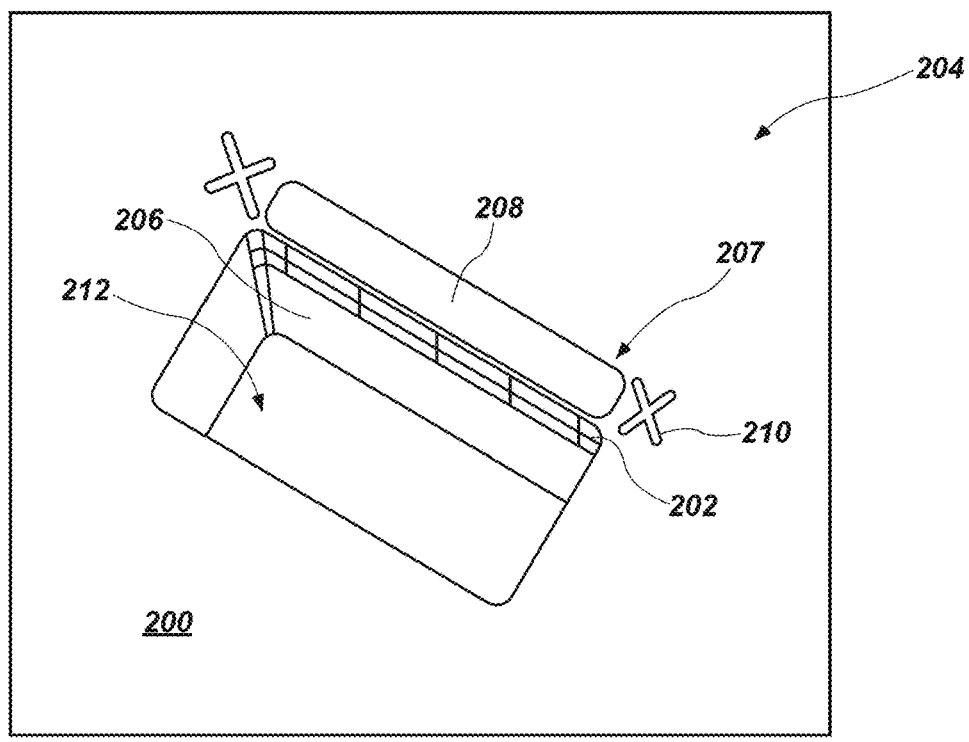
Figure 2C:
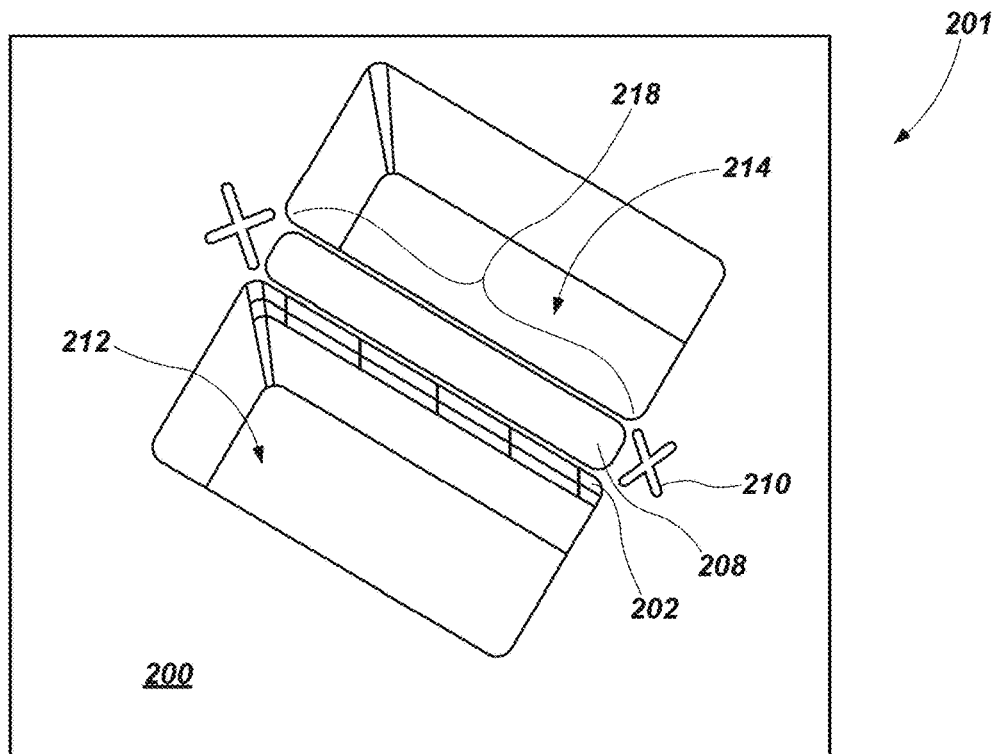
Figure 2D:
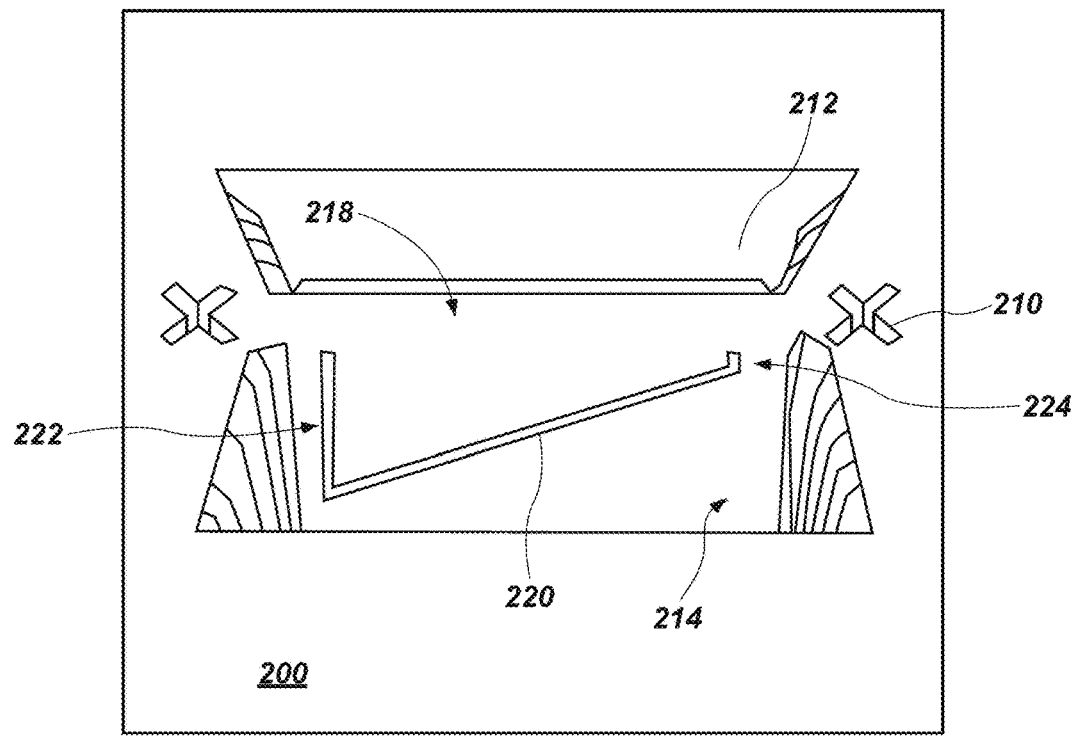
Figure 2E:
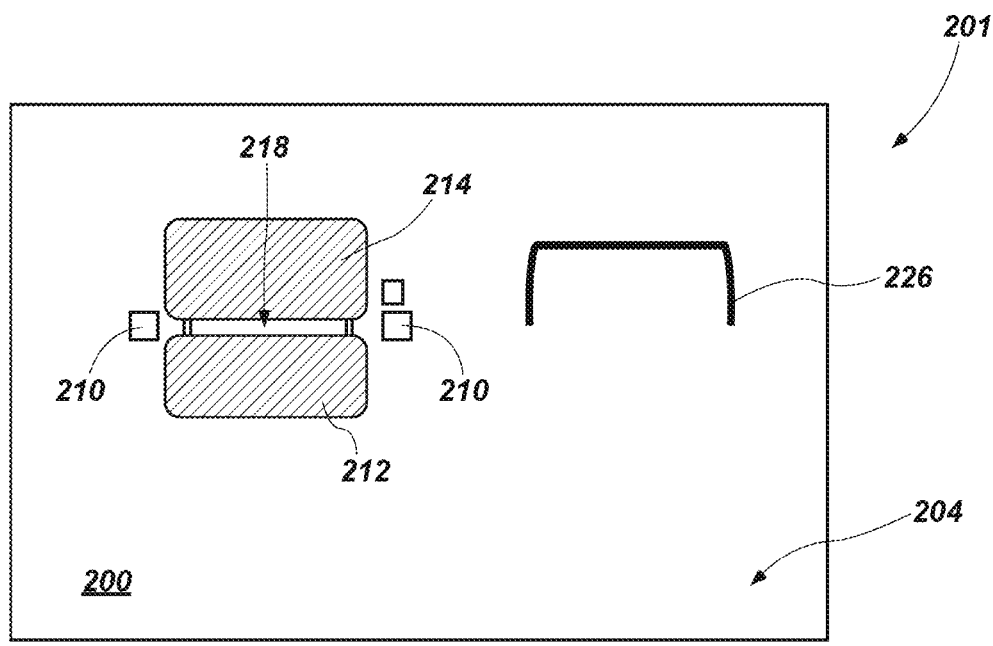
Figure 2F:
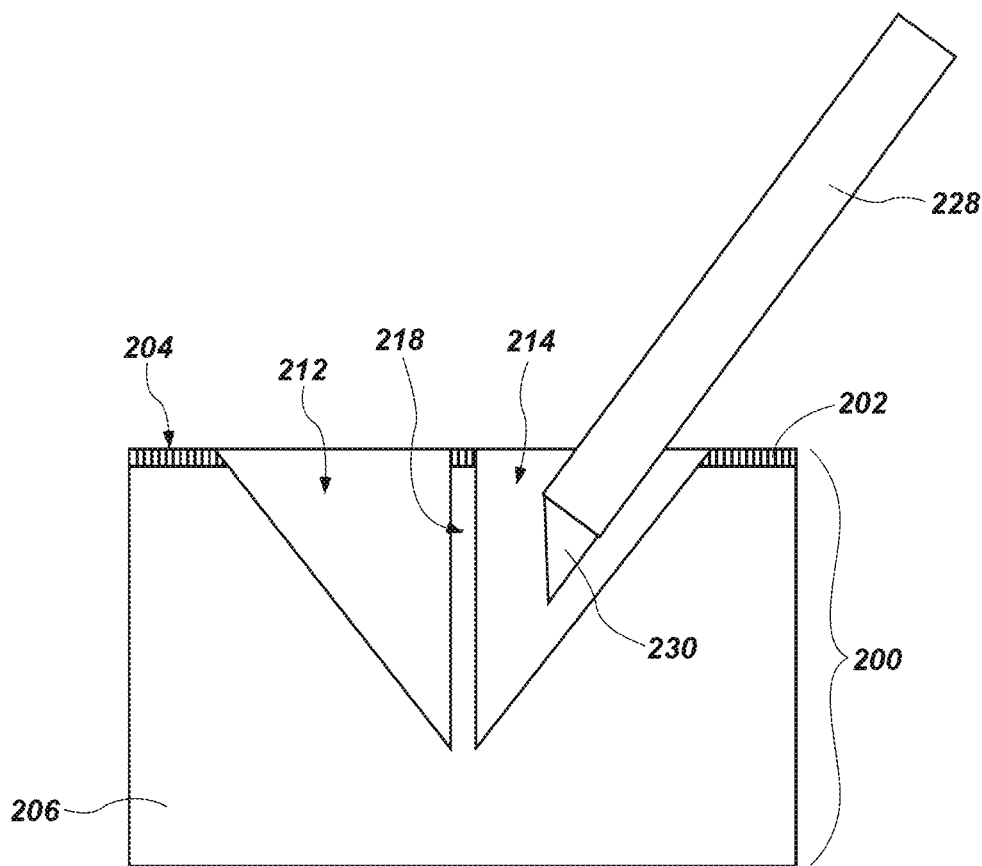
Figure 2G:
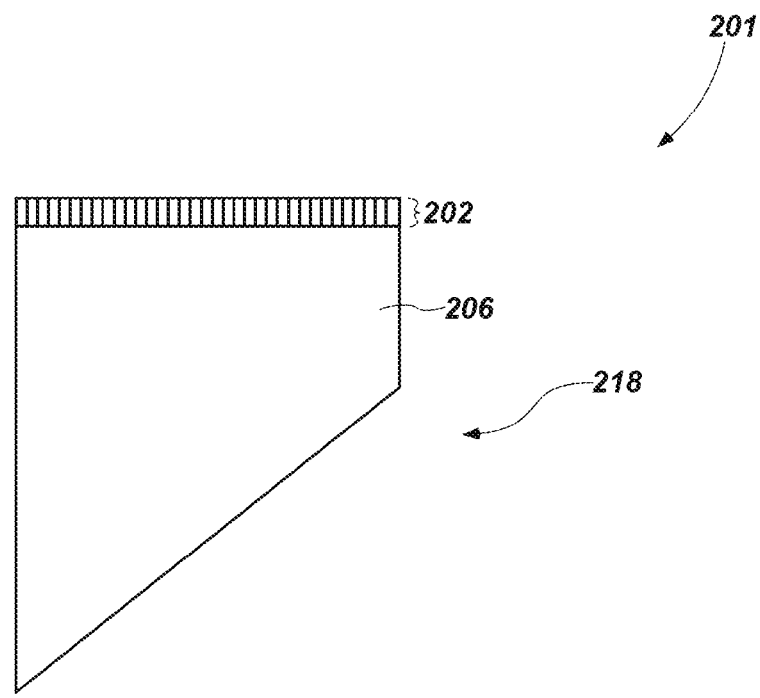
Figure 2H:
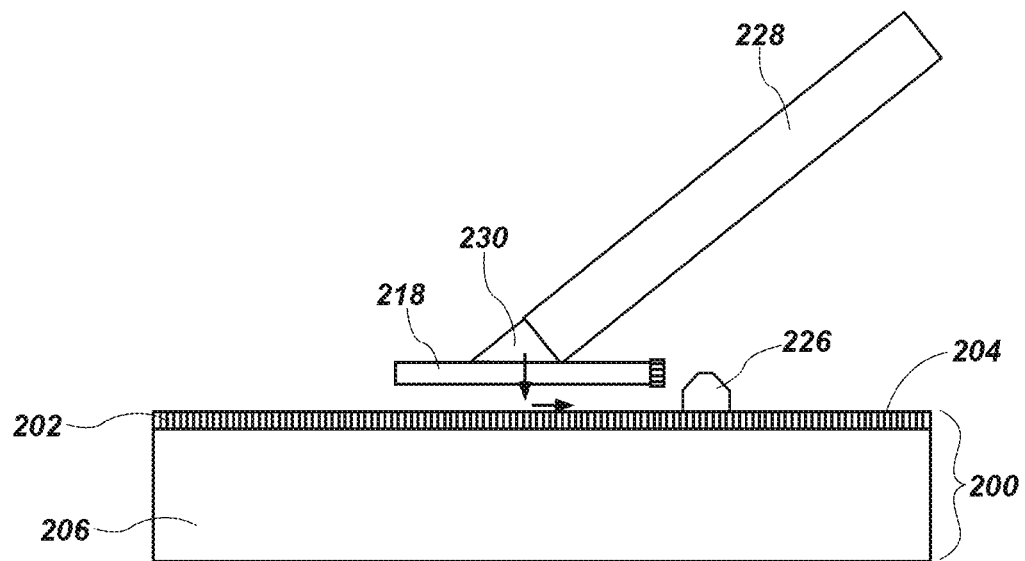
Figure 2I:
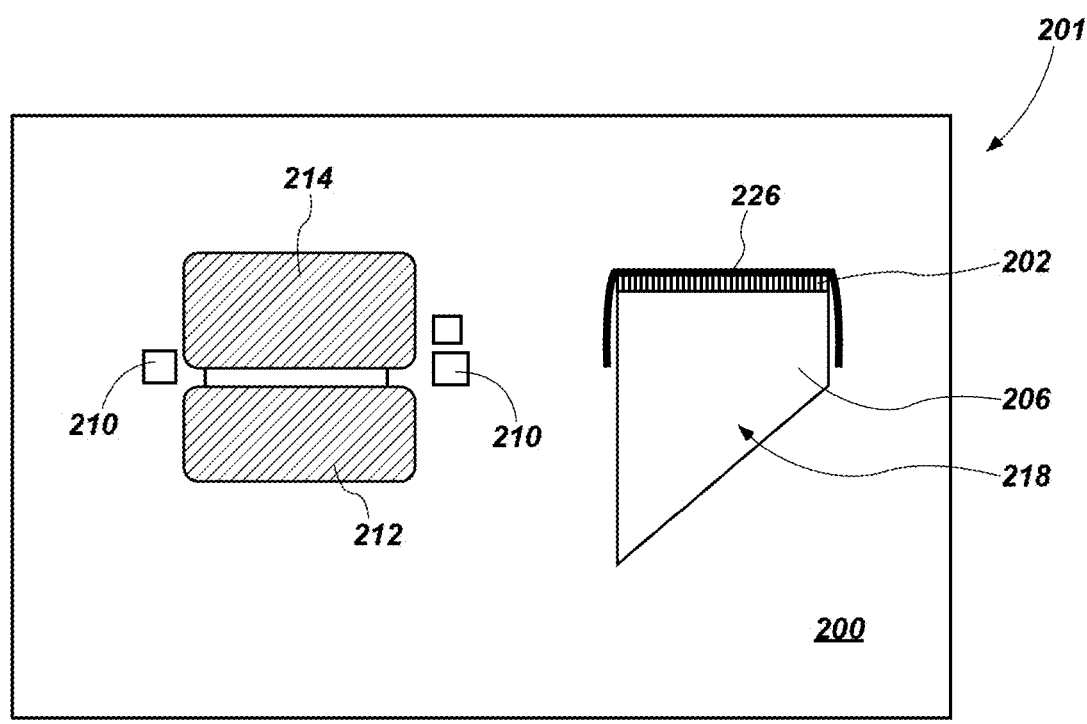
Figure 2J:
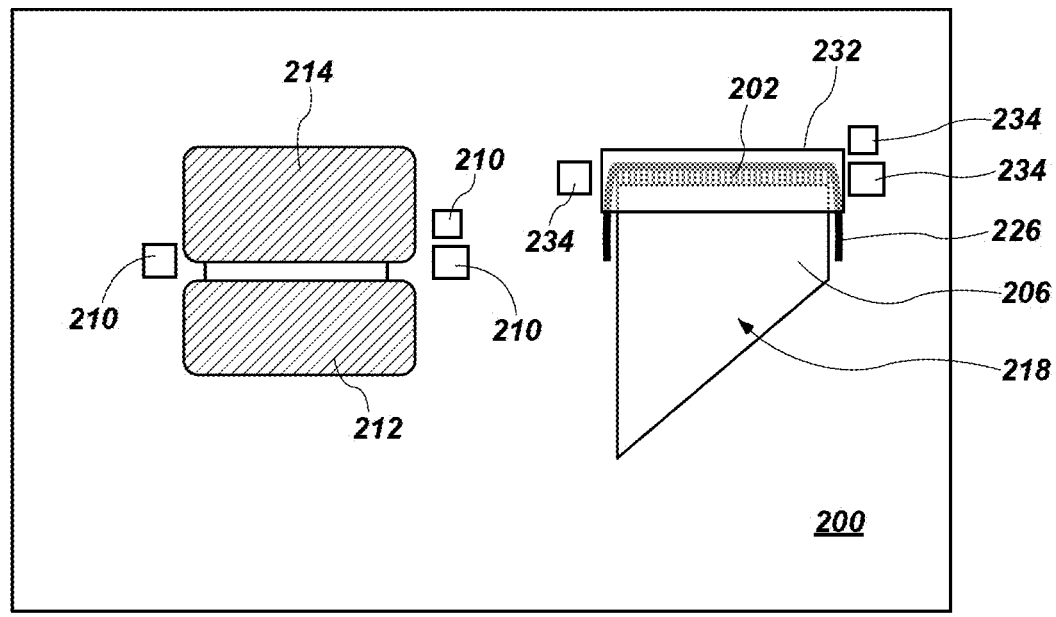
Figure 2K:
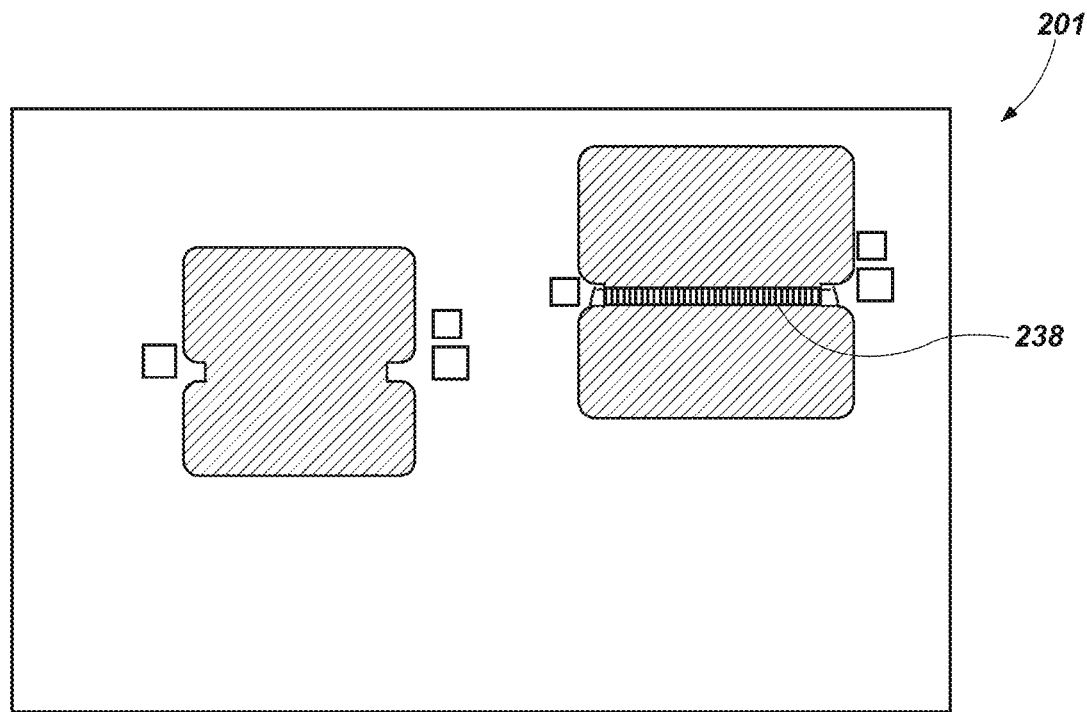
Figure 2L:
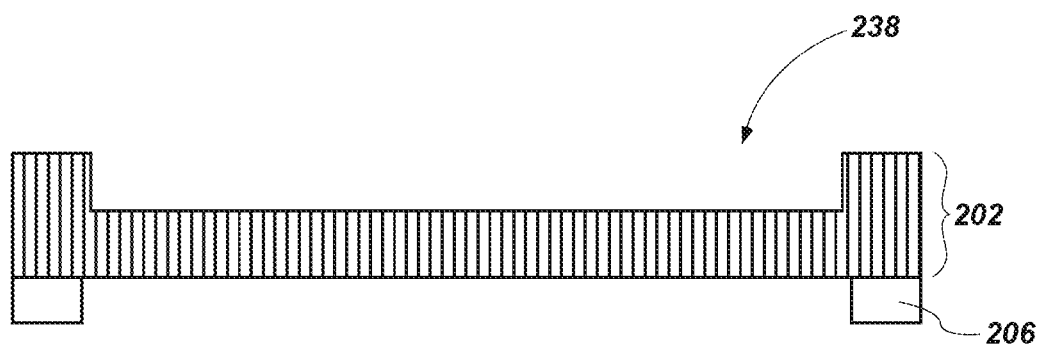
Figure 2M:
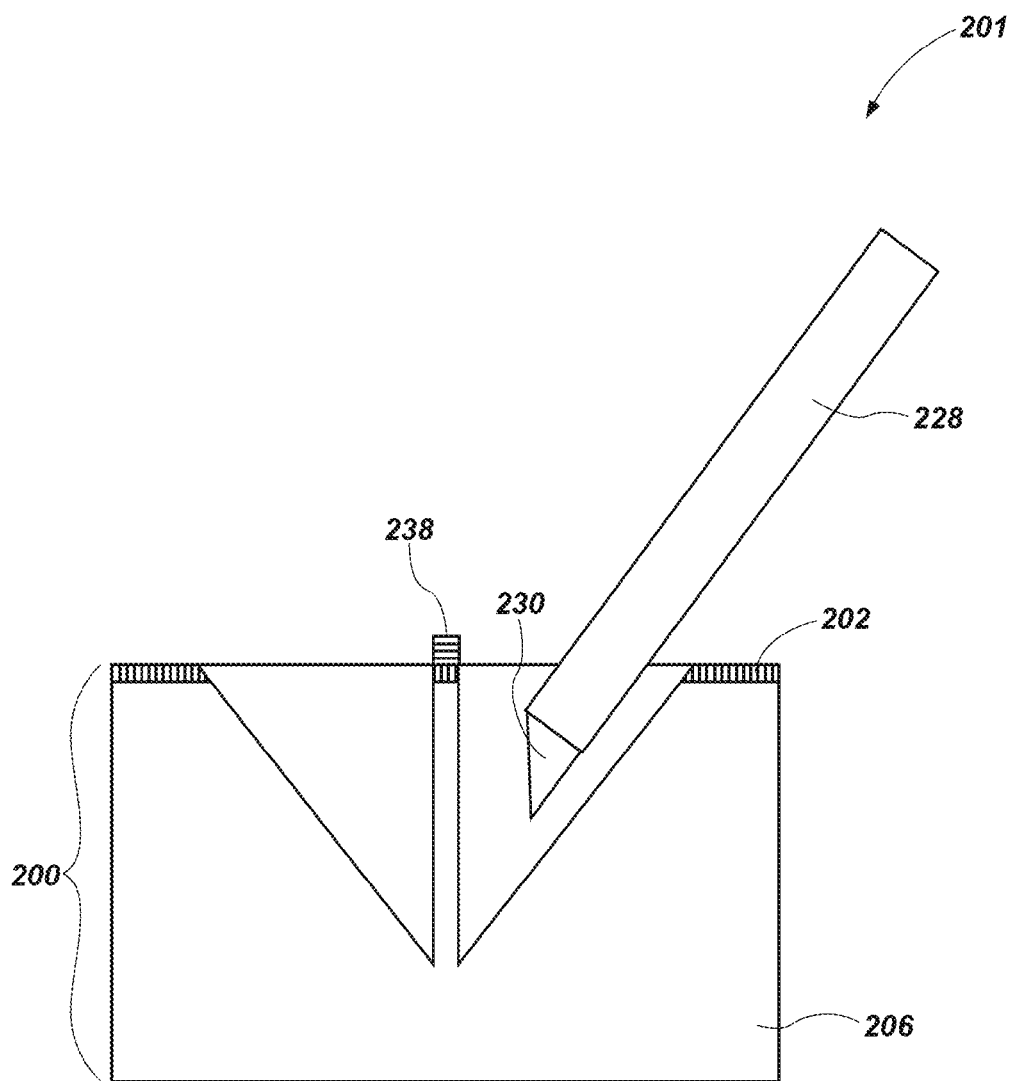
Figure 2N:
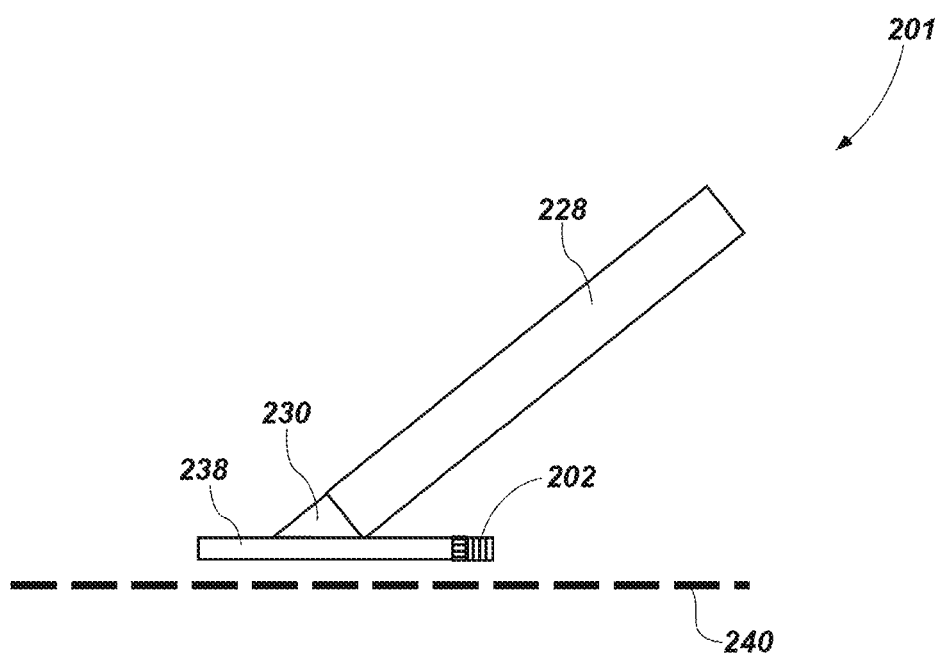

FIG. 1 is a schematic depiction of a dual beam system 110 that may be utilized to perform acts described herein in regard to FIGS. 2A-2N. In some embodiments, the dual beam system 110 may be used to perform the acts with a vertically mounted SEM (e.g., a longitudinal axis of the SEM is oriented in a vertical direction) column and a focused ion beam ("FIB") column mounted at an angle of approximately 45 degrees from a vertical longitudinal axis of the vertically mounted SEM. In some embodiments, the dual beam system 110 may comprise a commercially available dual beam system from, for example, Thermo Fisher Scientific Company, Hillsboro, Oreg. For instance, the dual beam system 110 may comprise the Thermo Fisher Scientific ExSolve DualBeam™ system. As another example, the dual beam system 110 may include the dual beam system 110 described in U.S. Patent Publication No. 2017/0250055A1, to Keady et al., filed May 15, 2017. While an example of a dual beam system 110 is described below, the disclosure is not limited and the processes described herein may be implemented with other dual beam systems and/or ion beam systems.

In some embodiments, the dual beam system 110 may include a scanning electron microscope 141 and a power supply and control unit 145. In operation, the electron microscope 141 may emit an electron beam 143 from a cathode 152 by applying voltage between the cathode 152 and an anode 154. In one or more embodiments, the electron beam 143 may be focused to a relatively fine spot via a condensing lens 156 and an objective lens 158. Furthermore, the electron beam 143 may be scanned two-dimensionally on a specimen via a deflection coil 160. The power supply and control unit 145 may control operation of the condensing lens 156, the objective lens 158, and the deflection coil 160.

In one or more embodiments, the dual beam system 110 may further include a lower chamber 126 housing a substrate 122, a movable X-Y stage 125, and one or more TEM sample holders 124. The substrate 122 may be disposed on the movable X-Y stage 125. In some embodiments, the substrate 122 may include one or more of a semiconductor device, a wafer, and a sample. The one or more TEM sample holders 124 may be disposed on (e.g., supported by) the movable X-Y stage 125. In operation and is described below, lamellae may be milled within the substrate 122 and may be extracted from the substrate 122 and moved to a TEM sample holder 124. Furthermore, in some embodiments, the movable X-Y stage 125 may be movable in a horizontal plane (X and Y axes) and vertically along a vertical axis (Z axis). Additionally, the movable X-Y stage 125, which may also be characterized as a support or a support surface, may be tilted and rotated about the Z axis. In some embodiments, a separate TEM sample stage (not shown) can be used. Such a TEM sample stage will also be moveable in the X, Y, and Z axes. In one or more embodiments, the dual beam system 110 may include a door 161 that may be opened for inserting a substrate 122 onto X-Y stage 125. The door 161 may be interlocked so that the door 161 cannot be opened if the dual beam system 110 is under vacuum.

In operation, the dual beam system 110 may focus the electron beam 143 onto the substrate 122. When electrons in the electron beam 143 strike (e.g., hit) the substrate 122, secondary electrons are emitted, as is known in the art. The secondary electrons may be detected by a secondary electron detector 140, as is discussed in greater detail below. For instance, a STEM detector 162 may be located beneath a TEM sample holder 124 and the X-Y stage 125 and may collect electrons that are transmitted through a sample mounted on the TEM sample holder 124.

The dual beam system 110 may also include a focused ion beam ("FIB") system 111. The FIB system 111 may include an ion column 112, an upper neck portion 113, and a focusing column 116. The ion column 112 may include an ion source 114, an extraction electrode 115, a focusing element 117, deflection elements 120, and a focused ion beam 118. The ion source 114 of the ion column 112 and the focusing column 116 may be at least partially disposed within the upper neck portion 113 of the FIB system 111. As noted above, a longitudinal axis of the FIB system 111 (i.e., the focusing column 116) is oriented at a 45-degree angle from the longitudinal axis of the scanning electron microscope 141. In operation, the focused ion beam 118 passes from the ion source 114 through the focusing column 116 and between the electrostatic deflection elements 120 toward the substrate 122 disposed on the movable X-Y stage 125 within the lower chamber 126 of the dual beam system 110. When the ion beam 118 strikes the substrate 122, material of the substrate 122 may be sputtered and physically ejected, from the substrate 122. As will be discussed in greater detail below, in some embodiments, the ion beam 118 may be utilized to prepare lamellae from the substrate 122. Alternatively, the ion beam 118 can be utilized to decompose a precursor gas to deposit a material, as is described in greater detail below.

The dual beam system 110 may include an ion pump 168 for evacuating one or more portions of the FIB system 111.

Additionally, the dual beam system 110 may include a turbomolecular and mechanical pumping system 130 operably coupled to and controlled by a vacuum controller 132 for evacuating the lower chamber 126. In some embodiments, the turbomolecular and mechanical pumping system 130 under the direction of the control of a vacuum controller 132 may provide a vacuum of between approximately 1×10−7 Torr (1.3×10−7 mbar) and 5×10−4 Torr (6×10−4 mbar) within the lower chamber 126. As will be understood by one of ordinary skill in the art, if an etch-assisting gas, an etch-retarding gas, or a deposition precursor gas is used, the lower chamber's 126 background pressure may rise to about 1×10−5 Torr (1.3×10−5 mbar).

The dual beam system 110 may further include a high voltage power supply 134 that provides an appropriate acceleration voltage to electrodes in ion beam focusing column 116 for energizing and focusing the ion beam 118. The high voltage power supply 134 may be connected to a liquid metal ion source 114 and to appropriate electrodes in the ion beam focusing column 116 for forming an approximately 1 keV to 60 keV ion beam 118 and directing the ion beam 118 toward the substrate 122.

Additionally, the dual beam system 110 may include a deflection controller and amplifier 136 and a pattern generator 138. The deflection controller and amplifier 136 may be operably coupled to the pattern generator 138. Furthermore, the deflection controller and amplifier 136 may be operably coupled to the deflection elements 120. As such, the ion beam 118 may be controlled manually and/or automatically to trace out a corresponding pattern on an upper surface 204 of substrate 122. In some embodiments, the dual beam system 110 may operate the deflection controller and amplifier 136 in accordance with a prescribed pattern provided by the pattern generator 138. In some embodiments, the deflection elements 120 may be disposed before the final lens along a direction in which the ion beam 118 is directed, as is known in the art. As is understood in the art, in some embodiments, beam blanking electrodes within ion beam focusing column 116 may cause the ion beam 118 to impact onto a blanking aperture instead of substrate 122 when a blanking controller applies a blanking voltage to the blanking electrode.

The liquid metal ion source 114 may provide a metal ion beam of gallium. The liquid metal ion source 114 may be capable of being focused into a sub one-tenth micrometer wide beam at the substrate 122 for either modifying the substrate 122 by ion milling, enhanced etch, material deposition, or for the purpose of imaging the substrate 122.

In some embodiments, the dual beam system 110 may further include a charged particle detector 140. In one or more embodiments, the charged particle detector 140 may include an Everhart Thornley or multi-channel plate and may be used for detecting secondary ion or electron emission. The charged particle detector 140 may be connected to a video circuit 142, which supplies drive signals to video monitor 144 and receives deflection signals from a system controller 119. The orientation and location of the charged particle detector 140 within the lower chamber 126 may vary in different embodiments. For example, a charged particle detector 140 may be coaxial with the ion beam 118 and may include a hole for allowing the ion beam 118 to pass therethrough. In other embodiments, secondary particles can be collected through a final lens and then diverted off axis for collection.

Additionally, the dual beam system 110 includes a micromanipulator 147 for precisely moving object within a vacuum chamber within the lower chamber 126. In some embodiments, the micromanipulator 147 may include an AutoProbe 200™ from Omniprobe, Inc., Dallas, Tex., or Model MM3A from Kleindiek Nanotechnik, Reutlingen, Germany. In additional embodiments, the micromanipulator 147 may form at least a portion of a TEMlink™ (i.e., a TEMLink™ TEM Lamella Extraction Station). In further embodiments, the micromanipulator 147 may include a TFS EZlift. In one or more embodiments, the micromanipulator 147 may include one or more precision electric motors 148 positioned outside the vacuum chamber of the lower chamber 126 to provide X, Y, Z, and theta control of a portion 149 positioned within the vacuum chamber of the lower chamber 126. The micromanipulator 147 may be fitted with different end effectors for manipulating small objects. For instance, in some embodiments, the micromanipulator 147 may include an end effector include a thin probe 150 (e.g., a thin glass probe). In other embodiments, the micromanipulator 147 may be separate from a TEMlink™, which may be used in conjunction with the dual beam system 110 to manipulate samples (e.g., lamellae) formed from the substrate 122.

The dual beam system 110 may further include a gas delivery system 146 extending into the lower chamber 126. The dual beam system 110 may utilize the gas delivery system 146 to introduce and direct a gaseous vapor toward the substrate 122. For instance, the gas delivery system 146 may include any of the gas delivery systems described in U.S. Pat. No. 5,851,413, to Casella et al., issued on Dec. 22, 1998. In additional embodiments, the gas delivery system 146 may include any of the gas delivery systems described in U.S. Pat. No. 5,435,850, to Rasmussen, issued Jun. 25, 1995. In some embodiments, the dual beam system 110 may utilize the gas delivery system 146 to deliver iodine to the substrate 122 to enhance etching. In additional embodiments, the dual beam system 110 may utilize the gas delivery system 146 to deliver a metal organic compound or metal on the substrate 122. As will be described in greater detail below, the dual beam system 110 may utilize the gas delivery system 146 to deposit a carbon nest 226 on the wafer 200 and/or fiducial markers 210 on the wafer 200.

The system controller 119 may control the operations of the various parts of the dual beam system 110. For instance, via the system controller 119, an operator may cause the ion beam 118 and/or the electron beam 143 to be scanned in a desired manner through commands entered into a conventional user interface. For instance, an operator may utilize the system controller 119, user interface, and video monitor 144 (e.g., display) to input one or more parameters of a procedure (e.g., recipe) to perform with the dual beam system 110. Alternatively, the system controller 119 may control the dual beam system 110 in accordance with programmed instructions. In some embodiments, the dual beam system 110 incorporates image recognition software. For instance, the dual beam system 110 may include software commercially available from Cognex Corporation, Natick, Mass., to automatically identify regions of interest. Additionally, system controller 119 can cause the dual beam system 110 to manually or automatically extract samples in accordance with the embodiments described herein. For example, the system controller 119 may automatically locate similar features on semiconductor wafers including multiple devices, and take samples of those features on different (or the same) devices.

FIGS. 2A-2N show a process 201 through which a planar view STEM image may be acquired utilizing the dual beam system 110 (e.g., the Thermo Fisher Scientific ExSolve DualBeam™) described above in regard to FIG. 1. In other words, the process 201 may be utilized to achieve a STEM image that depicts internal structures of a wafer as if viewed from a plane parallel to an upper surface of the wafer. The process 201 may include loading a wafer 200 into the dual beam system 110 to create (e.g., ion mill) an initial lamella 218 (referred to hereinafter as the "initial lamella 218") from the wafer 200. In some embodiments, the wafer 200 may include an upper portion 202 proximate to an upper surface 204 of the wafer 200 and a bulk silicon base portion 206 beneath the upper portion 202. As will be understood in the art, the upper portion 202 may include features (e.g., internal structures) of interest, and STEM images of those features may be desirable to determine a quality of the wafer 200, defects in the wafer 200, etc. As a non-limiting example, the wafer 200 may include an upper portion 202 comprising an active surface comprising integrated circuitry in the form of semiconductor devices as known in the art.

Referring to FIG. 2A, in some embodiments, when creating the initial lamella 218, the dual beam system 110 may deposit a protective layer 208 of a material such as tungsten over a region of interest 207 on the upper surface 204 of the wafer 200 (i.e., where the initial lamella 218 will be milled) using the electron beam or the ion beam deposition methods described above in regard to FIG. 1. For instance, the dual beam system 110 may deposit the protective layer 208 utilizing either the electron beam 143 or the focused ion beam 118. In some embodiments, the dual beam system 110 may deposit the protective layer 208 utilizing the gas delivery system 146 in any of the manners for depositing materials described above in regard to FIG. 1. In other embodiments, the process 201 may not include depositing a protective layer 208. In other words, not every embodiment described herein requires depositing of a protective layer 208. Additionally, the process 201 may include depositing one or more fiducial markers 210 to identify a milling site of the initial lamella 218 and to assist in orienting the focused ion beam 118 of the dual beam system 110 during a milling operation. In some embodiments, an operator of the dual beam system 110 may input parameters of an overall milling procedure (e.g., a recipe) via the user interface described above to cause the dual beam system 110 to deposit the protective layer 208 and/or the fiducial markers 210 according to the input parameters.

In reference to FIGS. 2B and 2C, the process 201 may include utilizing the focused ion beam 118 of the dual beam system 110 and using a relatively high beam current with a corresponding relatively large beam size to mill relatively large amounts of material away from a front portion and a back portion of the region of interest 207 to form two milled trenches 212 and 214. In some embodiments, the two milled trenches 212 and 214 may have a generally rectangular prism shape. In other embodiments, the two milled trenches 212 and 214 may have generally triangular prism shapes among others. Regardless, remaining material between the two milled trenches 212 and 214 may form a thin, at least substantially vertical, sample section, i.e., a portion of the initial lamella 218, which includes the region of interest 207. In some embodiments, the angle of the focused ion beam 118 used in the milling is generally angled at 90° from the upper surface 204 of the wafer 200. This allows for the focused ion beam 118 to mill vertically into wafer 200. In other embodiments, the focused ion beam 118 may be oriented at a 45 degree angle from a vertical access and may be utilized to form triangular prism trenches. In one or more embodiments, forming the initial lamella 218 may not include any cleaning actions and/or thinning processes, which are known and conventionally performed in the art. In other words, the initial lamella 218 may be left intentionally thick. In other embodiments, forming the initial lamella 218 may include cleaning actions, but the initial lamella 218 may still be left intentionally thick. In some embodiments, an operator of the dual beam system 110 may input parameters of the overall milling procedure (e.g., a recipe) via the user interface to cause the dual beam system 110 to mill the trenches 212 and 214 according to the input parameters.

Referring to FIG. 2D, after the two milled trenches 212 and 214 are formed, the wafer 200 and the X-Y stage 125 may be tilted and/or rotated and the dual beam system 110 may make a cut 220 at an angle partially along the perimeter of the initial lamella 218 utilizing the focused ion beam 118 and leaving the initial lamella 218 hanging by tabs at either side at a top of the lamella. In some embodiments, the cut 220 may create an asymmetrical lamella. For instance, the asymmetrical lamella may have a convex quadrilateral shape with one straight side 222 and one obtuse side 224. More specifically, the initial lamella 218 may be a right trapezoid with two parallel sides. For example, the initial lamella 218 may have the shape depicted in FIG. 2G (described below). As a non-limiting example, the initial lamella 218 may include any of the asymmetrical lamellae described in U.S. Pat. No. 8,884,247, to Miller et al., issued Nov. 11, 2014. As is known in the art, asymmetrical lamellae may assist in identifying regions of interest more readily and quickly. In other embodiments, the cut 220 may have a general U-shape and may create a general symmetrical lamella. In view of the foregoing, one of ordinary skill in the art will recognize that the initial lamella 218 may be formed via any manner known in the art absent cleaning processes and/or thinning process. For instance, the initial lamella 218 may be formed via any of the manners described in U.S. Pat. No. 8,884,247, to Miller et al. In some embodiments, an operator of the dual beam system 110 may input parameters of the overall milling procedure (e.g., a recipe) via the user interface to cause the dual beam system 110 to make the cut 220 according to the input parameters.

In reference to FIG. 2E, prior to and/or after making the cut 220 in the initial lamella 218, the process 201 may include creating a nest 226 near the milling site of the initial lamella 218. For instance, the dual beam system 110 may utilize either the focused ion beam 118 or the electron beam 143 along with the gas delivery system 146 to deposit a nest 226 adjacent to the milling site of the initial lamella 218 on an upper surface 204 of the wafer 200. For instance, the dual beam system 110 may deposit the nest 226 via any of the manners described above in regard to depositing materials utilizing the gas delivery system 146. In some embodiments, the nest 226 may be sized and shaped to receive an upper portion 202 (i.e., a rectangular portion) of the initial lamella 218, as is described in greater detail below. For instance, the nest 226 may have a general U-shape. In some embodiments, the nest 226 may include a carbon material (e.g., graphite and/or amorphous carbon). In other embodiments, the nest 226 may include one or more of tungsten and tetraethyl orthosilicate ("TEOS"). In one or more embodiments, the nest 226 may have a U-shape or a right-angle shape. In additional embodiments, then nest 226 may include a relatively flat layer of material. As will be described in greater detail below, the nest 226 may serve to break an electrostatic connection between a probe (e.g., thin probe 150) and the initial lamella 218. In some embodiments, an operator of the dual beam system 110 may input parameters of the overall milling procedure (e.g., a recipe) via the user interface to cause the dual beam system 110 to create the nest 226 according to the input parameters. In other embodiments, the process 201 may not include creating and/or depositing a nest 226 near the milling site of the initial lamella 218. For example, not every embodiment described herein requires creating and/or depositing of the nest 226.

Referring to FIGS. 2F-2H, after forming the nest 226 on the upper surface 204 of the wafer 200, the process 201 may include cutting the tabs (which is known in the art), lifting (e.g., plucking, removing, etc.) the initial lamella 218 from the two milled trenches 212 and 214, and placing (e.g., disposing) the initial lamella 218 on the upper surface 204 of the wafer 200 proximate the nest 226 on the upper surface 204 of the wafer 200. In particular, FIG. 2F represents an action of lifting the initial lamella 218 from the wafer 200 with probe 228. FIG. 2G is a front view of the initial lamella 218. FIG. 2H represent an action of placing the initial lamella 218 back on the upper surface 204 of the wafer 200.

Referring to FIGS. 2F-2H together, the initial lamella 218 may be placed on the upper surface 204 of the wafer 200 unlike conventional processes, which typically include placing wafers on a grid. In some embodiments, the process 201 may include lifting and placing the initial lamella 218 with a probe 228, which, as noted above, may include probe 150. For instance, the process 201 may include lifting and placing the initial lamella 218 with a glass probe. In one or more embodiments, the process 201 may include lifting and placing the initial lamella 218 with a lamella extraction station (e.g., the micromanipulator 147). In some embodiments, the lamella extraction station may include a TEM-Link™ TEM lamella extraction station. For instance, the lamella extraction station may include a semi-automated full wafer TEM lamella lift out system. Although a specific system is identified for lifting and placing the initial lamella 218, the disclosure is not so limited; rather, any system known in the art for lifting (i.e., removing) and placing lamella may be utilized in the process 201. Also, as noted above, in some embodiments, the lamella extraction station may be a part of the dual beam system 110; and in other embodiments, the lamella extraction station may be separate from the dual beam system 110 but may be utilized in conjunction with the dual beam system 110.

In view of the foregoing, in some embodiments, the initial lamella 218 may be lifted from the wafer 200 and placed (e.g., disposed) back on the upper surface 204 of the wafer 200 outside of the dual beam system 110. For example, after the initial lamella 218 is formed, the wafer 200 may be unloaded from the dual beam system 110 and the lamella extraction station may be utilized to lift and place the initial lamella 218 external to the dual beam system 110. In other embodiments, the initial lamella 218 may be lifted from the wafer 200 and placed back on the upper surface 204 of the wafer 200 within the dual beam system 110. For instance, the lamella extraction station may form an integral part of the dual beam system 110 and may lift and place the initial lamella 218 within the dual beam system 110 without unloading the wafer 200.

In particular, the process 201 may include lifting the initial lamella 218 by positioning the probe 228 over and proximate to the initial lamella 218 and lowering and/or moving a probe tip 230 of the probe 228 into contact with the initial lamella 218. In some embodiments, the probe 150 may utilize electrostatic forces to attract the initial lamella 218 to the probe tip 230 and to grasp the initial lamella 218. In additional embodiments, the probe 150 may have a hollow center, and the probe 150 may utilize a vacuum created within the hollow center of the probe 150 to secure the initial lamella 218 to the probe tip 230.

Referring to FIGS. 2H and 2I together, upon securing the initial lamella 218 to the probe tip 230 of the probe 150, the process 201 may include lowering the probe 150 until the initial lamella 218 is placed on the upper surface 204 of the wafer 200 proximate to the nest 226 on the upper surface 204 of the wafer 200. For instance, the initial lamella 218 may be laid flat on the upper surface 204 of the wafer 200. As noted above, in some embodiments, the nest 226 may assist in breaking an electrostatic connection between the probe 150 and the initial lamella 218.

In one or more embodiments, the process 201 may include placing the initial lamella 218 on the upper surface 204 of the wafer 200 at a location proximate to the nest 226 and then sliding the initial lamella 218 along the upper surface 204 of the wafer 200 into the nest 226. For instance, the process may include utilizing the probe 150 to slide the initial lamella 218 up against the nest 226 until the nest 226 at least substantially surrounds an outer periphery of the upper portion 202 of the initial lamella 218. For instance, the process 201 may include aligning the initial lamella 218 within the nest 226. In other embodiments, the probe 150 may place the initial lamella 218 directly into the nest 226 such that the nest 226 at least substantially surrounds an outer periphery of the upper portion 202 of the initial lamella 218.

In some embodiments, disposing the initial lamella 218 directly into the nest 226 and/or sliding the initial lamella 218 may result in the initial lamella 218 not being aligned within the nest 226. For instance, the initial lamella 218 may be askew within the nest 226 and/or the focusing ion beam 118 (which is used to mill additional lamella (described below)) of the dual beam system 110. Accordingly, in one or more embodiments, the process may include adjusting and/or reorienting the initial lamella 218 with the probe 150 to properly align the initial lamella 218 and to ensure that the features of interest included within the upper portion 202 of the initial lamella 218 are included within the planar lamella (described below). In some instances, the initial lamella 218 may be adjusted and/or reoriented automatically by one or more of the lamella extraction station and the dual beam system 110. For instance, the position of the initial lamella 218 may be adjusted to align internal structures (i.e., the features of interest) within the upper portion 202 of the initial lamella with the focused ion beam 118 of the dual beam system 110. As is described in greater detail below in regard to FIGS. 4A-4E, in one or more embodiments, a window (e.g., milled out portion, a thinned portion, etc.) may be formed in the initial lamella 218 to expose internal structures (e.g., crystalline structures) of the initial lamella 218, and the internal structures may be utilized to align the initial lamella 218. In additional embodiments, the initial lamella 218 may be aligned on the upper surface 204 of the wafer 200 utilizing a tab formed in the nest 226 and a corresponding notch cut into a top of the initial lamella 218. In particular, the tab of the nest 226 may be inserted into the notch of the initial lamella 218 to align the initial lamella with the focused ion beam 118 of the dual beam system 110. In yet further embodiments, the initial lamella 218 may be aligned on the upper surface 204 of the wafer 200 utilizing a recess milled into the wafer 200. For instance, the recess may be formed in the shape of an outer peripheral edge of the initial lamella 218, and the initial lamella 218 may be placed within the recess to align the initial lamella with the focused ion beam 118 of the dual beam system 110.

Referring to FIGS. 2F-2I together, in one or more embodiments, as noted above, the initial lamella 218, which is milled from the wafer 200, may include the upper portion 202 and a bulk silicon base portion 206. Furthermore, the upper portion 202 may be at a top of the initial lamella 218. As also noted above the upper portion 202 may include features (e.g., internal structures, crystalline structures, etc.) of interest, and STEM images of those features may be desirable to determine a quality of the wafer 200, defects in the wafer 200, etc. Furthermore, as shown in FIG. 2I, in some embodiments, the upper portion 202 of the initial lamella 218 may be disposed against the nest 226. Moreover, as will be discussed in greater detail below, the upper portion 202 of the initial lamella 218 may be a targeted portion in creating a second lamella.

In embodiments where the wafer 200 is unloaded from the dual beam system 110, after placing the initial lamella 218 within the nest 226, the process 201 may include reloading the wafer 200 into the dual beam system 110. Furthermore, in reference to FIG. 2J, the process 201 may include depositing a material 232 to adhere the initial lamella 218 to the upper surface 204 of the wafer 200 and at least substantially hold the initial lamella 218 in place. In some embodiments, the material 232 may include tungsten, carbon, and/or TEOS. In one or more embodiments, the material 232 may be deposited utilizing the gas delivery system 146 of the dual beam system 110. Additionally, the process 201 may include depositing one or more fiducial markers 234 proximate to the initial lamella 218 and identifying an additional milling site on the wafer 200. As is known in the art, the fiducial markers 234 may be utilized by the dual beam system 110 for future processing (e.g., milling of a second lamella). For instance, the fiducial markers 234 may assist the dual beam system 110 in orienting and moving (e.g., scanning) the focused ion beam 118. The fiducial markers 234 may be deposited via the gas delivery system 146 of the dual beam system 110. In some embodiments, an operator of the dual beam system 110 may input parameters of an overall additional milling procedure (e.g., an additional recipe) via the user interface described above to cause the dual beam system 110 to deposit the material 232 and/or the fiducial markers 234 according to the input parameters of the additional milling procedure.

After the fiducial markers 234 have been deposited, with reference to FIG. 2K, the process 201 may include milling a second lamella (referred to hereinafter as the "planar lamella 238") to include at least a portion of the upper portion 202 of the initial lamella 218. Furthermore, the planar lamella 238 may be milled via any of the manners described above in regard to FIGS. 2A-2D. In some embodiments, an operator of the dual beam system 110 may input parameters of the overall additional milling procedure (e.g., an additional recipe) via the user interface described above to cause the dual beam system 110 to mill the planar lamella 238 according to the input parameters of the additional milling procedure.

Referring to FIG. 2L, in some embodiments, milling the planar lamella 238 may further include thinning the planar lamella 238 with the focused ion beam 118. For instance, the dual beam system 110 may thin the planar lamella 238 utilizing the focused ion beam 118. As a non-limiting example, the planar lamella 238 may be thinned via any of the manners known in the art. Furthermore, milling the planar lamella 238 may, optionally, include any cleaning processes known in the art. In some embodiments, an operator of the dual beam system 110 may input parameters of the overall additional milling procedure (e.g., an additional recipe) via the user interface described above to cause the dual beam system 110 to thin the planar lamella 238 according to the input parameters of the additional milling procedure.

In reference to FIGS. 2M and 2N, after milling the planar lamella 238, the process 201 may include lifting the planar lamella 238 from the second milling site and placing the planar lamella 238 on an amorphous carbon grid 240 for imaging with a TEM and/or STEM. For example, the process 201 may include lifting the planar lamella 238 via any of the methods described above in regard to FIG. 2F. Furthermore, the process 201 may include placing the planar lamella 238 on the amorphous carbon grid 240 via any of the methods described above in regard to FIG. 2H. As will be understood in the art, the amorphous carbon grid 240 may assist in breaking any electrostatic connection between the probe 150 and the planar lamella 238.

After placing the planar lamella 238 on the amorphous carbon grid 240, the process 201 may include imaging and performing metrology on the planar lamella 238 via TEM and/or STEM systems. For instance, the process 201 may include performing automated imaging and metrology utilizing a Thermo Scientific Metrios™ system. Although specific TEM and STEM imaging/metrology systems are described herein, the disclosure is not so limited, and the process 201 may include imaging and/or performing metrology analysis via any TEM and/or STEM system known in the art.

Figure 3:
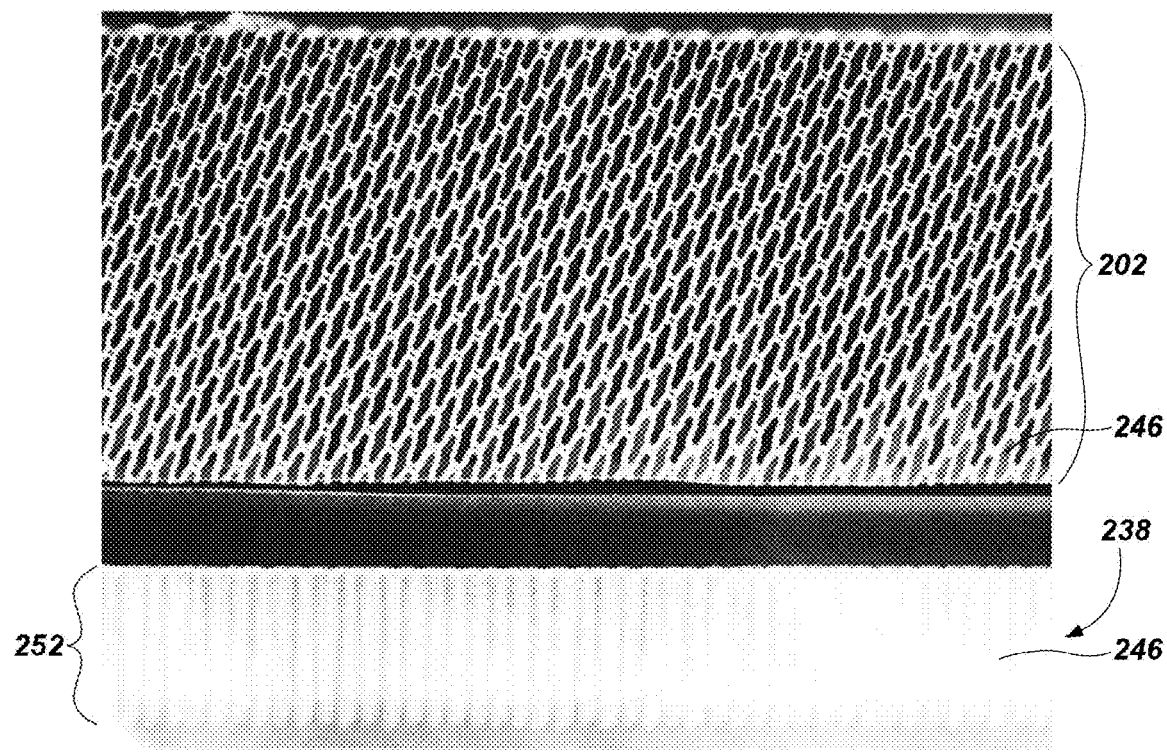
FIG. 3 is an image of a sample of a semiconductor device according to one or more embodiments of the present disclosure.

FIG. 3 shows an example image obtained via STEM imaging that includes the upper portion 202 of the initial lamella 218 along with a respective upper portion 252 of the planar lamella 238. As shown, because the initial lamella 218 was milled, placed on its side on the upper surface 204 of the wafer 200, milled again as a portion of the planar lamella 238, and then placed on the amorphous grid, when the planar lamella 238 and, specifically, the portion of the planar lamella 238 including the upper portion 202 of the initial lamella 218 is imaged, a planar cross-section view of the initial lamella 218 is achieved that is not achievable utilizing conventional operations of the dual beam system 110. For instance, the planar lamella 238 includes a first cross-sectional view of internal structures 246 of the wafer 200 within the portion of the planar lamella 238 not comprised of the initial lamella 218, and a second cross-sectional view of the internal structures 246 that is orthogonal to the first cross-sectional view within the portion of the planar lamella 238 comprising the initial lamella 218. The first cross-sectional view may include a view depicting internal structures 246 as if viewed from a plane orthogonal to the upper surface 204 of the wafer 200, and the second cross-sectional view may include a view depicting internal structures 246 as if viewed from a plane parallel to the upper surface 204 of the wafer 200. Conventional methods utilizing the dual beam system 110 only achieve the first cross-sectional view.

Furthermore, because the process 201 described herein provides both the first cross-sectional view and the second cross-sectional view, the process 201 may provide more complete images of the internal structures of the wafer 200 in comparison to conventional methods only include the first cross-sectional view. As a result, the process 201 may provide more complete information regarding the internal structures of the wafer 200. Accordingly, a more complete analysis can be achieved utilizing the process 201 described herein in comparison to conventional processes. Due to the more complete analysis, a quality of the wafer 200 and devices formed thereon may be better determined, which results in better products and more flaws detected.

Figure 4A:
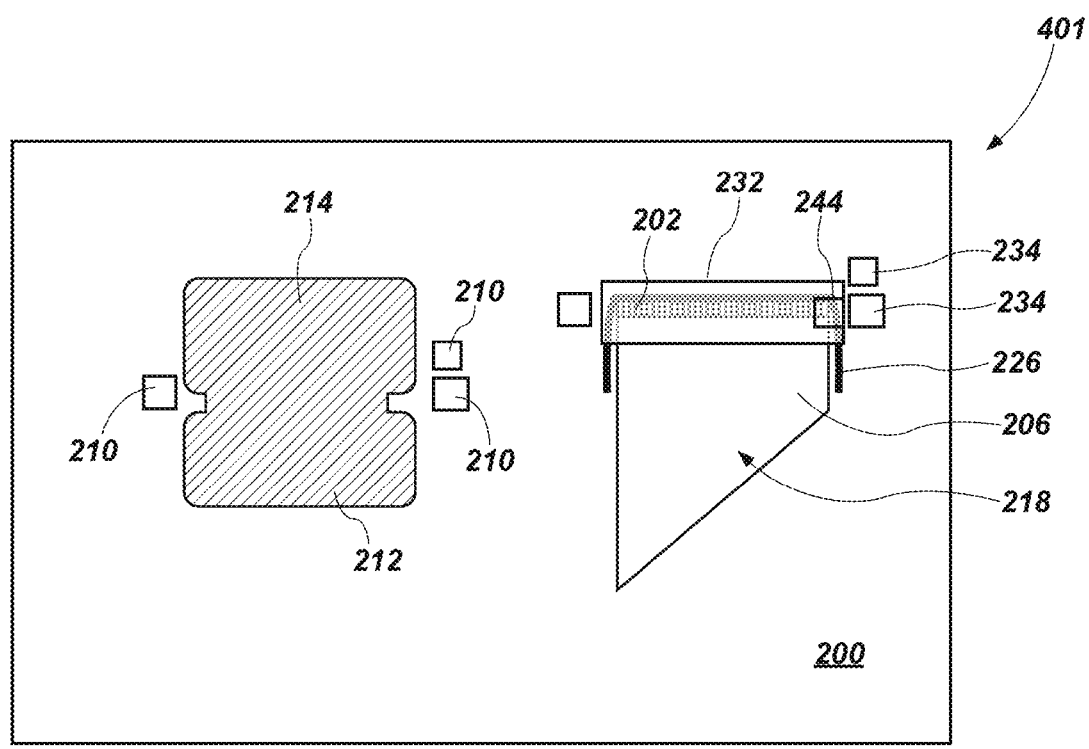
FIGS. 4A-4E illustrate another process for preparing a sample of a semiconductor device for TEM and/or STEM imaging according to one or more embodiments of the present disclosure.
Figure 4B:
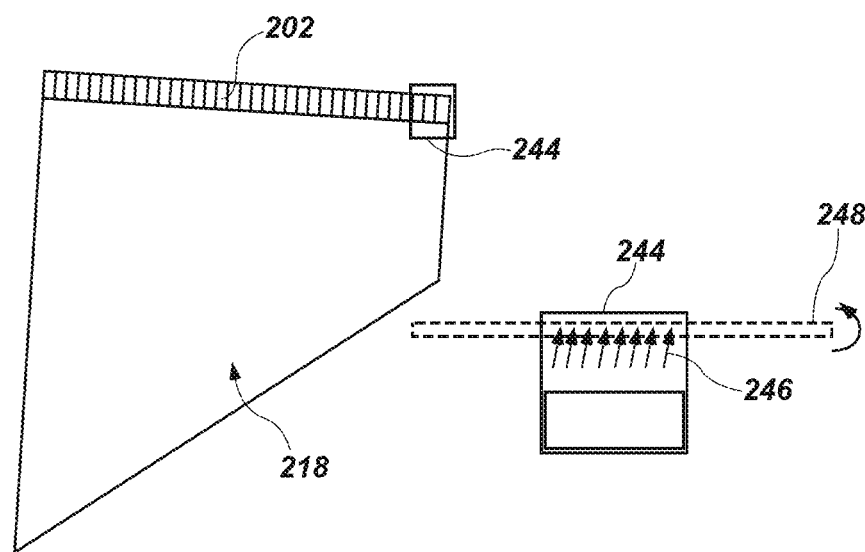
Figure 4C:
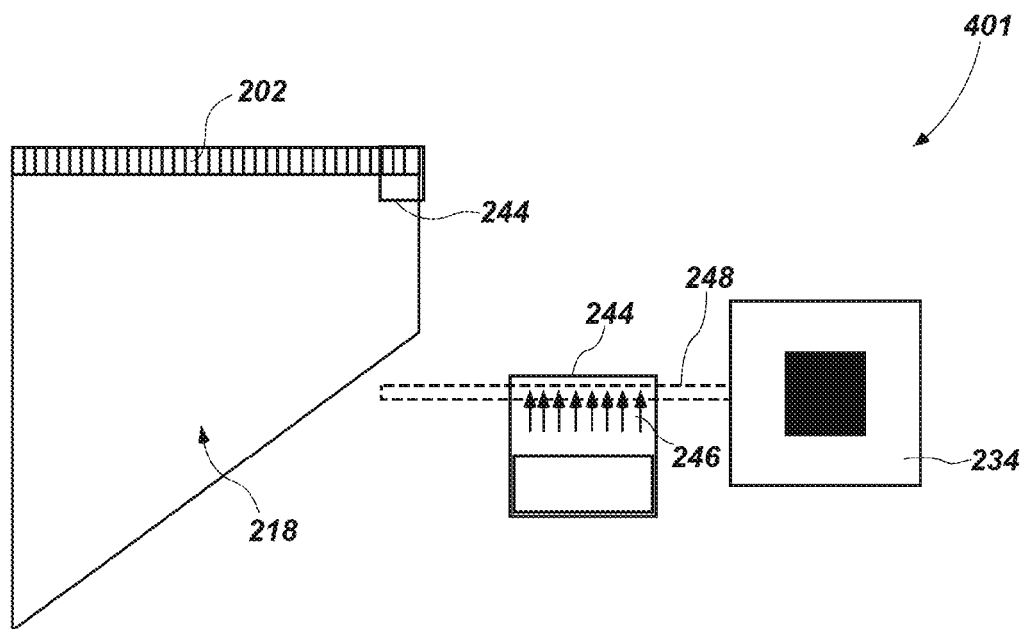

FIGS. 4A-4E represent an additional process 401 that can be utilized in conjunction with the process 201 described above to align the initial lamella 218 on the upper surface 204 of the wafer 200 and for subsequent milling. In some embodiments, the process 401 can take place after depositing the material 232 over the initial lamella 218. Referring to FIGS. 4A-4C together, which show the initial lamella 218 disposed within the nest 226, in some embodiments, the process 401 may include milling a window 244 within the initial lamella 218. As used herein, the term "window" may include a recess formed within the lamella and exposing internal structures of the lamella. Furthermore, the window 244 may be milled utilizing the focused ion beam 118 of the dual beam system 110 via any of the methods described above in regard to FIGS. 1-2N. In some instances, the milling the window 244 may include milling the window 244 at least partially within (e.g., to include at least a portion of) the upper portion 202 of the initial lamella 218. Milling the window 244 within the upper portion 202 of the initial lamella 218 may expose the internal structures 246 (e.g., features of interest) of the initial lamella 218. As will be appreciated by one of ordinary skill in the art, in some embodiments, the internal structures 246 may be oriented relative to one another in at least substantially parallel lines.

Accordingly, once the window 244 in milled within the initial lamella 218, the process 401 may include determining if the internal structures 246 are oriented as desired relative to the wafer 200, the nest 226, and/or a desired planar lamella 238 thickness and placement (referred to as "248" within FIG. 4B). In some embodiments, the internal structures 246 of the initial lamella 218 may need to be aligned with the focusing ion beam 118 to achieve an optimal image of the later-to-be-formed planar lamella 238. In other words, the internal structures 246 and/or the orientation of the internal structures 246 need to form a zero-degree angle with a direction in which the focusing ion beam 118 translates (e.g., moves). In some embodiments, the dual beam system 110 may utilize pattern recognition and edge finding software to determine the positions and orientations of the internal structures 246, and as a result, the overall initial lamella 218 on the upper surface 204 of the wafer 200. For instance, the dual beam system 110 may utilize pattern recognition and edge finding software to determine the position of the internal structures and as a result, the initial lamella 218, in each of the three axes (X, Y, and Z). Additionally, based on the determined locations and orientations of the internal structures 246 and initial lamella 218, the dual beam system 110 determines an amount of rotation needed in each of the three axes to properly align the initial lamella with the focused ion beam 118 of the dual beam system 110. Furthermore, based on the determined amount of rotation, the dual beam system 110 and/or operator may utilize the micromanipulator 147 to rotate the initial lamella 218 to achieve proper alignment with the focused ion beam 118 of the dual beam system 110. In other embodiments, the initial lamella 218 may be left as is, and the focusing ion beam 118 can be rotated instead to align the focusing ion beam 118 with the internal structures 246. As will be described in greater detail below, in some embodiments, the dual beam system 110 may further utilize pattern recognition and edge finding software to determine a location of the bulk silicon base portion 206 of the initial lamella 218 within the Y-axis to utilize in forming an additional window in the bulk silicon base portion 206.

Figure 4D:
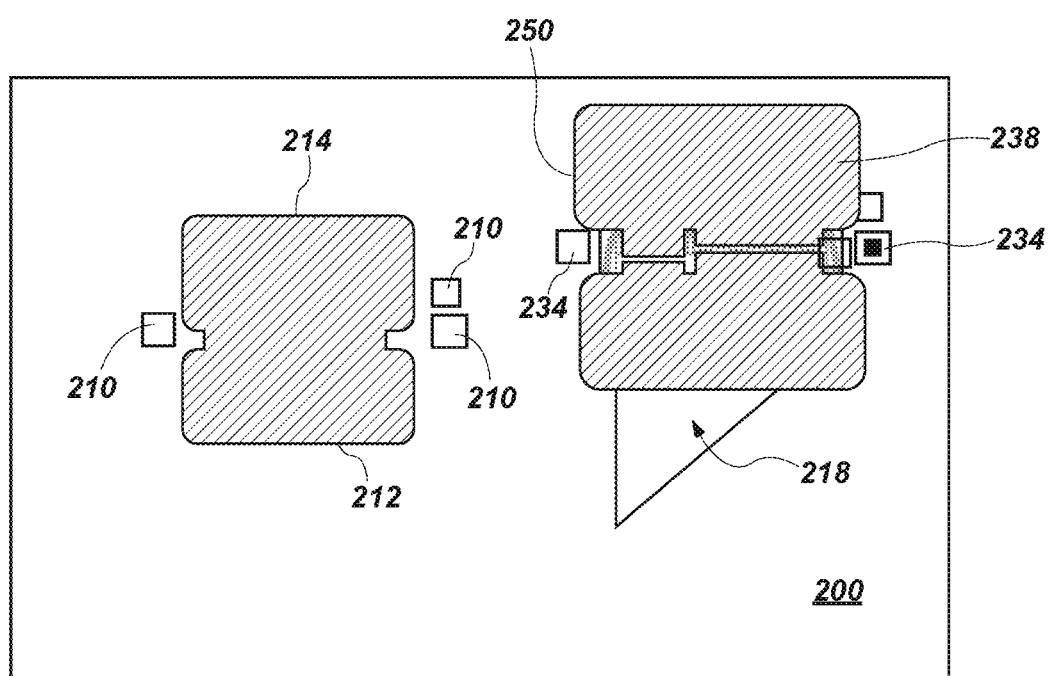
Figure 4E:
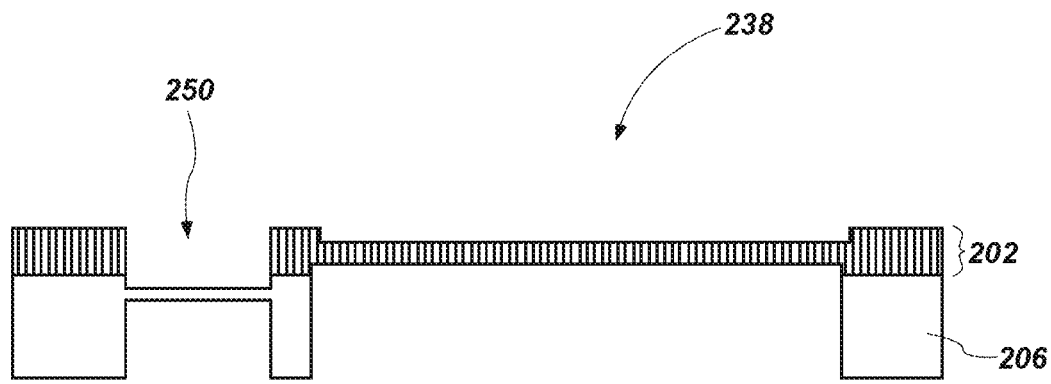

Referring to FIGS. 4C and 4D together, once the initial lamella 218 is properly oriented, the process 401 may include depositing one or more fiducial markers 234 relative to the initial lamella 218 via any of the methods described above in regard to FIG. 2A. In some embodiments, placement of the fiducial markers 234 may be determined based on location of the internal structures 246 within the Y-axis, determined above in regard to FIGS. 4A and 4B. Furthermore, the process 401 may include milling the planar lamella 238 via any of the methods described above in regard to FIG. 2K. Moreover, referring to FIG. 4E, the process 401 may include thinning the planar lamella 238 via any of the methods described above in regard to FIG. 2L. However, the process 401 may further include forming an additional window 250 within the bulk silicon portion of the initial lamella 218 within the planar lamella 238. For instance, in typical processes, the planar lamella 238 may be thinned about a central longitudinal axis of the upper portion 202 of the initial lamella 218 in order to ensure that the planar lamella 238 includes the features of interest included within the upper portion 202 of the initial lamella 218. However, according to the process 401, a portion of the planar lamella 238 may be thinned about an axis extending through the bulk silicon base portion 206 of the initial lamella 218 (i.e., the region of the initial lamella 218 below the upper portion 202) to form the additional window 250 such that, when thinned, the bulk silicon is exposed on both lateral sides of the planar lamella 238 within the additional window 250.

In some embodiments, the additional window 250 within the bulk silicon base portion 206 of the initial lamella 218 within the planar lamella 238 may assist in aligning the planar lamella 238 with TEM beams of the TEM and/or STEM imaging systems described above. For instance, the TEM and/or STEM system may utilize the pattern recognition and edge finder software described above to determine a lattice structure of the bulk silicon base portion 206 of the initial lamella 218 and may correctly align the planar lamella 238 with respect to the electron beam (for imaging). In some embodiments, the TEM and/or STEM system analyzes a diffraction pattern of the lattice structure of the bulk silicon base portion 206 within the additional window 250 and determines, based on the foregoing analysis, required tilts (e.g., a and 0 tilts) to center the pattern of the lattice structure about a zone axis. Creating the additional window 250 in the bulk silicon base portion 206 of the initial lamella 218 provides advantages over conventional methods. For instance, lamellae milled via conventional methods do not include the additional window because the lamellae do not include any portion of an initial lamella. As a result, the diffraction pattern of the lattice structure of the bulk silicon cannot be used to align the lamellae. As will be understood by one of ordinary skill in the art, the planar lamella 238 may be lifted, placed, and imaged via any of the methods described above in regard to FIGS. 2M, 2N, and 3.

Figure 5:
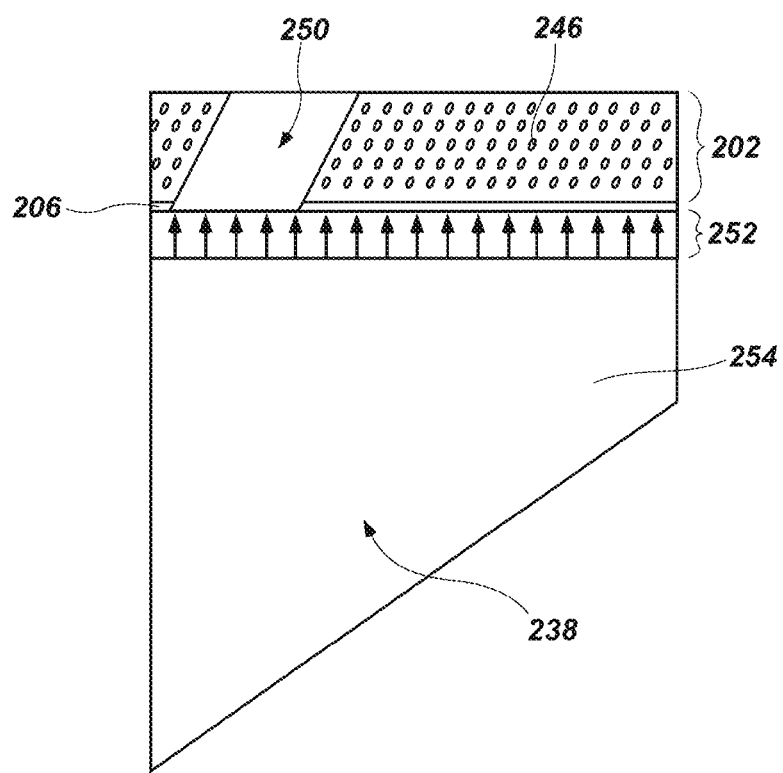
FIG. 5 shows a front view of a planar lamella prepared via one or more of the processes described herein.

FIG. 5 shows a front view of a planar lamella 238 formed via process 201 and process 401. As shown, the planar lamella 238 may include the upper portion 202 of the initial lamella 218 providing a planar view of the features of interest (e.g., internal structures) of the wafer 200. The planar lamella 238 may further include the additional window 250 formed in the bulk silicon base portion 206 of the initial wafer 200. The planar lamella 238 may also include a respective upper portion 252 below the initial lamella 218 including features of interest of the wafer 200 that can be view from an angle orthogonal to the planar view of the initial wafer 200. Additionally, the planar lamella 238 may include the respective bulk silicon base portion 254.

Figure 6A:
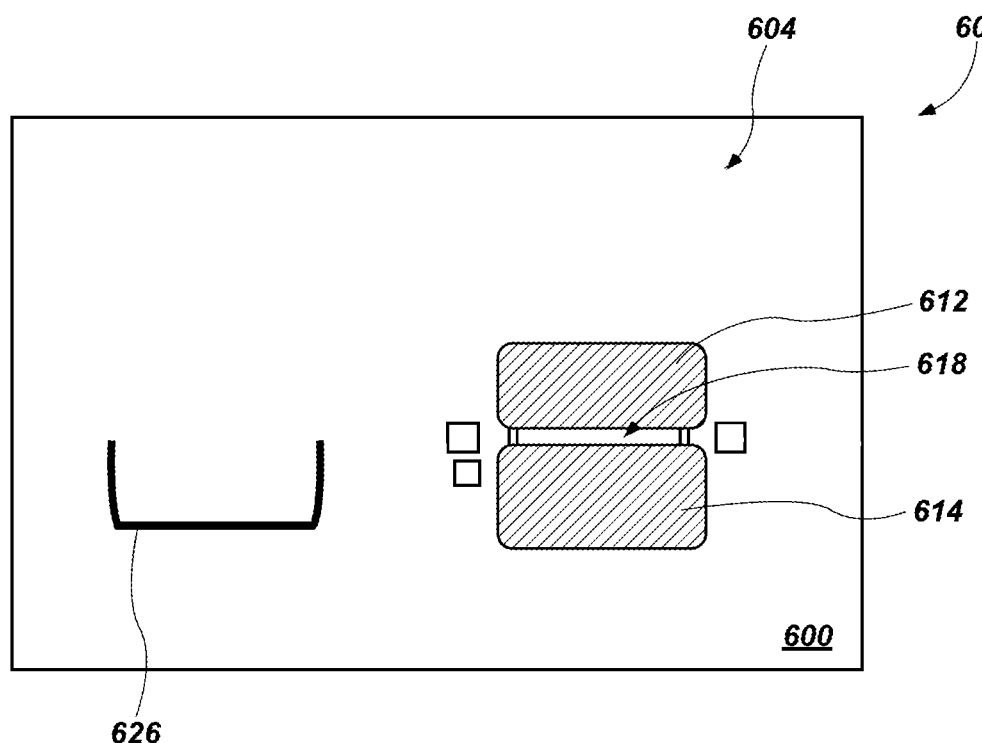
FIGS. 6A-6J illustrate acts of a process for preparing a sample of a semiconductor device for TEM and/or STEM imaging according to one or more embodiments of the present disclosure.

FIGS. 6A-6J show a process 601 through which a planar view STEM image may be acquired utilizing the dual beam system 110 described above in regard to FIG. 1. In particular, FIGS. 6A-6N show a process 601 for acquiring a planar view STEM image of a lamella having tall features of interest (e.g., tall internal structures) that are typically outside of a usable range for a conventional dual beam system 110.

The process 601 may include forming an initial relatively deep lamella 618 (referred to hereinafter as an "initial deep lamella 618") via any of the processes described above in regard to FIGS. 2A-2D. For example, the process 601 may include forming an initial deep lamella 618 having a depth within a range of about 4 µm and about 6 µm. Furthermore, the initial deep lamella 618 may have a relatively thick upper portion 602 of features of interest (e.g., tall internal structures). For instance, the upper portion 602 may have a thickness within a range of about 2 µm and about 3 µm. Furthermore, the initial deep lamella 618 may be left intentionally thick.

In reference to FIG. 6A, the process 601 may include creating a nest 626 near the milling site of the initial deep lamella 618. As described above in regard to FIG. 2E, the dual beam system 110 may utilize either the focused ion beam 118 or the electron beam 143 along with the gas delivery system 146 to deposit a nest 626 adjacent to the milling site of the initial deep lamella 618 on an upper surface 604 of the wafer 600. For instance, the dual beam system 110 may deposit the nest 626 via any of the manners described above in regard to depositing materials utilizing the gas delivery system 146. In some embodiments, the nest 626 may be sized and shaped to receive the upper portion 602 (i.e., a rectangular portion) of the initial deep lamella 618, as is described in greater detail below. For instance, the nest 626 may have a general U-shape or a right-angle shape. In some embodiments, the nest 626 may include any of the materials described above in regard to FIG. 2E. In additional embodiments, the nest 626 may include a relatively flat layer of material. Also, as described above, the nest 626 may serve to break an electrostatic connection between a probe (e.g., thin probe 150) and the initial deep lamella 618. Furthermore, as described above, an operator of the dual beam system 110 may input parameters of the overall milling procedure (e.g., a recipe) via the user interface to cause the dual beam system 110 to create the nest 626 according to the input parameters. In other embodiments, the process 601 may not include creating and/or depositing a nest 626 near the milling site of the initial deep lamella 618. For example, not every embodiment described herein requires creating and/or depositing of the nest 626.

Figure 6B:
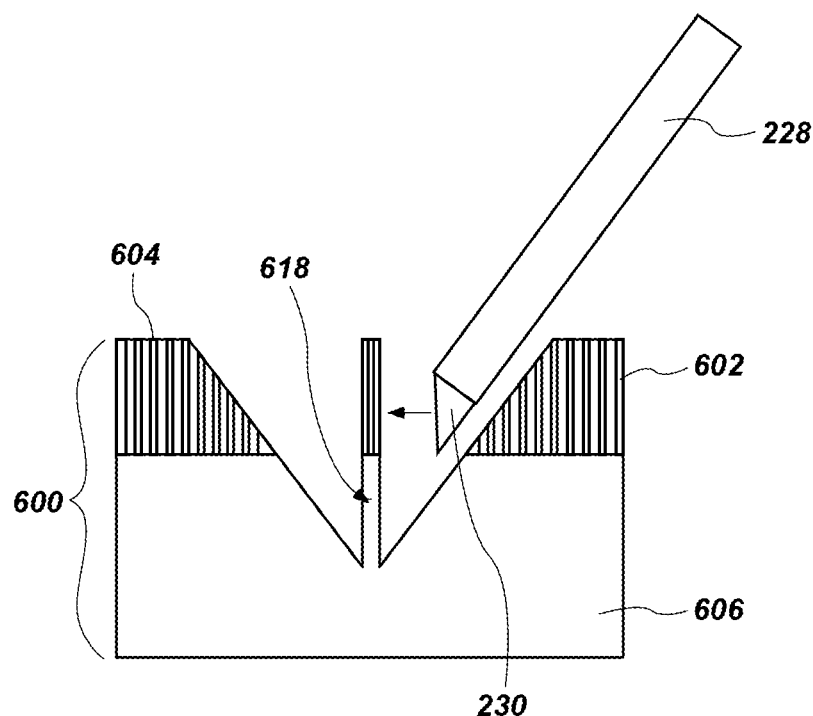
Figure 6C:
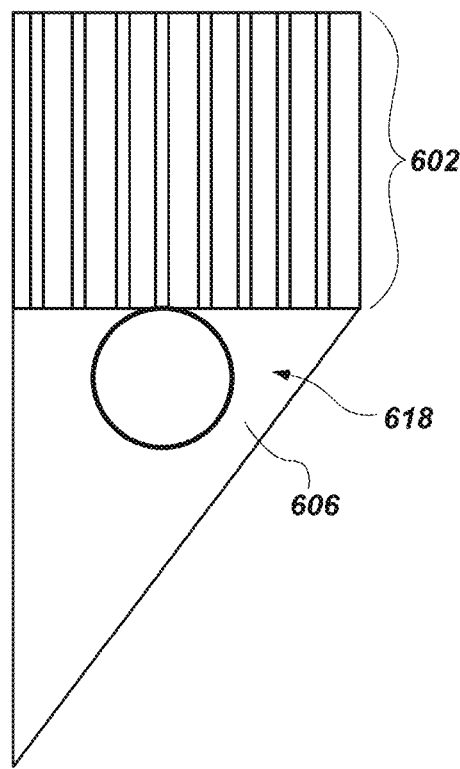
Figure 6D:
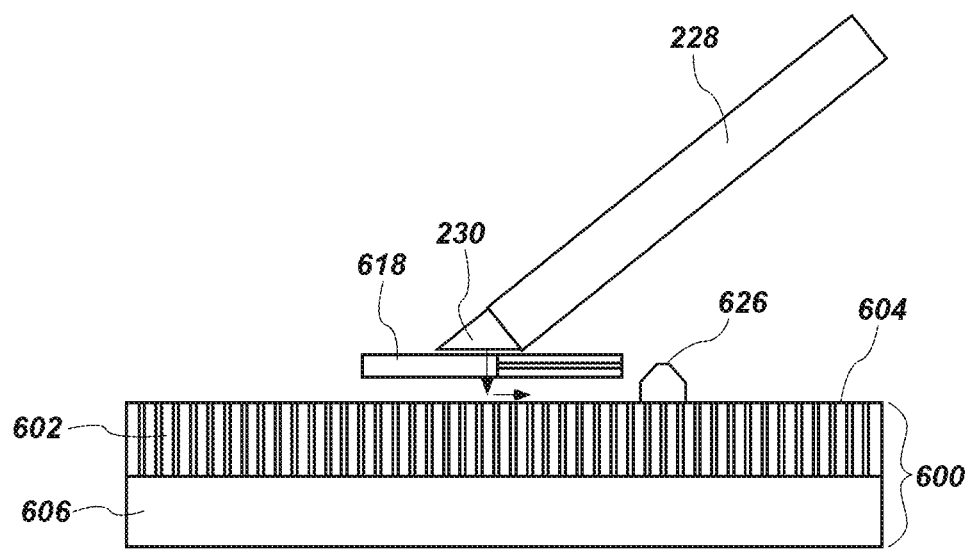

Referring to FIGS. 6B-6D, after forming the nest 626 on the upper surface 604 of the wafer 600, the process 601 may include cutting the tabs, lifting (e.g., plucking, removing, etc.) the initial deep lamella 618 from the two milled trenches 612 and 614, and placing (e.g., disposing) the initial deep lamella 618 on the upper surface 604 of the wafer 600 proximate the nest 626 on the upper surface 604 of the wafer 600. In particular, FIG. 6B represents an action of lifting the initial deep lamella 618 from the wafer 600 with probe 228. FIG. 6C is a front view of the initial deep lamella 618. FIG. 6D represent an action of placing the initial deep lamella 618 back on the upper surface 604 of the wafer 600.

The initial deep lamella 618 may be placed on the upper surface 604 of the wafer 600 unlike conventional processes, which typically include placing wafers on a grid. In some embodiments, the process 601 may include lifting and placing the initial deep lamella 618 with a probe 228, which may include probe 150. For instance, the process 601 may include lifting and placing the initial deep lamella 618 with a glass probe. In one or more embodiments, the process 601 may include lifting and placing the initial deep lamella 618 with a lamella extraction station (e.g., the micromanipulator 147). In some embodiments, the lamella extraction station may include a TEMLink™ TEM lamella extraction station. For instance, the lamella extraction station may include a semi-automated full wafer TEM lamella lift out system. Although a specific system is identified for lifting and placing the initial deep lamella 618, the disclosure is not so limited; rather, any system known in the art for lifting (i.e., removing) and placing lamella may be utilized in the process 601. Also, as noted above, in some embodiments, the lamella extraction station may be a part of the dual beam system 110; and in other embodiments, the lamella extraction station may be separate from the dual beam system 110 but may be utilized in conjunction with the dual beam system 110.

In view of the foregoing, in some embodiments, the initial deep lamella 618 may be lifted from the wafer 600 and placed (e.g., disposed) back on the upper surface 604 of the wafer 600 outside of the dual beam system 110. For example, after the initial deep lamella 618 is formed, the wafer 600 may be unloaded from the dual beam system 110 and the lamella extraction station may be utilized to lift and place the initial deep lamella 618 external to the dual beam system 110. In other embodiments, the initial deep lamella 618 may be lifted from the wafer 600 and placed back on the upper surface 604 of the wafer 600 within the dual beam system 110. For instance, the lamella extraction station may form an integral part of the dual beam system 110 and may lift and place the initial deep lamella 618 within the dual beam system 110 without unloading the wafer 600.

In particular, the process 601 may include lifting the initial deep lamella 618 by positioning the probe 228 over and proximate to the initial deep lamella 618 and lowering and/or moving a probe tip 230 of the probe 228 into contact with the initial deep lamella 618. In some embodiments, the probe 228 may utilize electrostatic forces to attract the initial deep lamella 618 to the probe tip 230 and to grasp the initial deep lamella 618. In additional embodiments, the probe 228 may have a hollow center, and the probe 228 may utilize a vacuum created within the hollow center of the probe 228 to secure the initial deep lamella 618 to the probe tip 230.

Figure 6E:
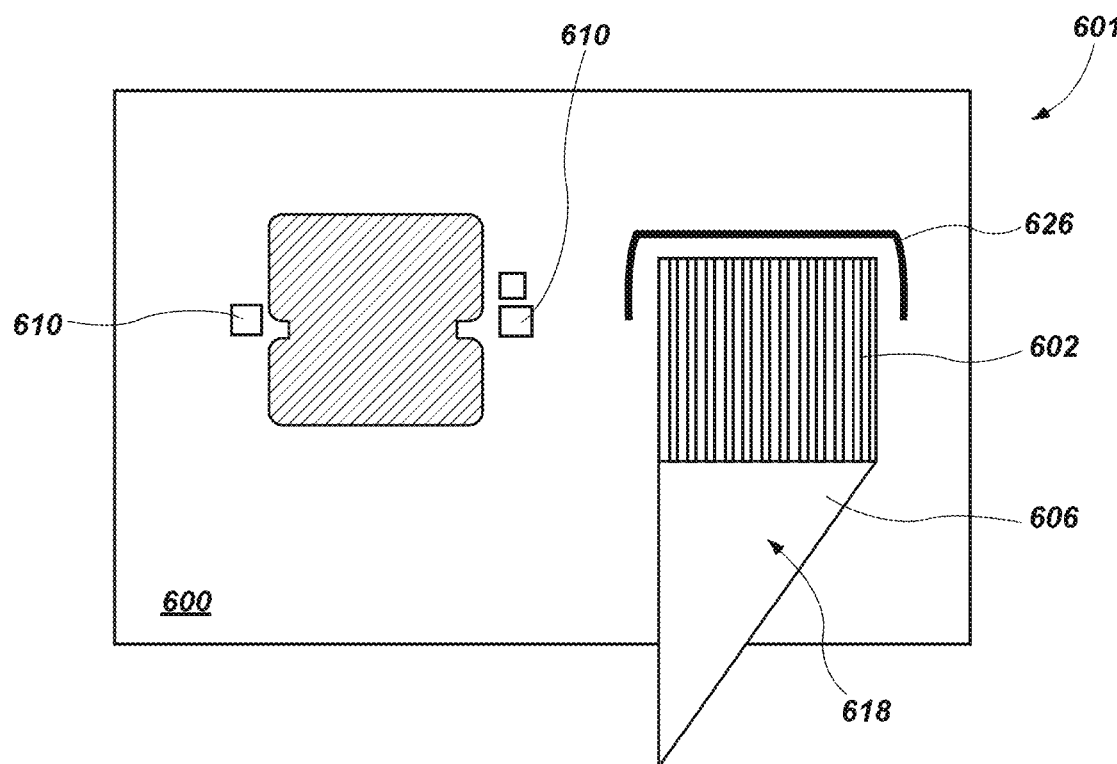
Figure 6F:
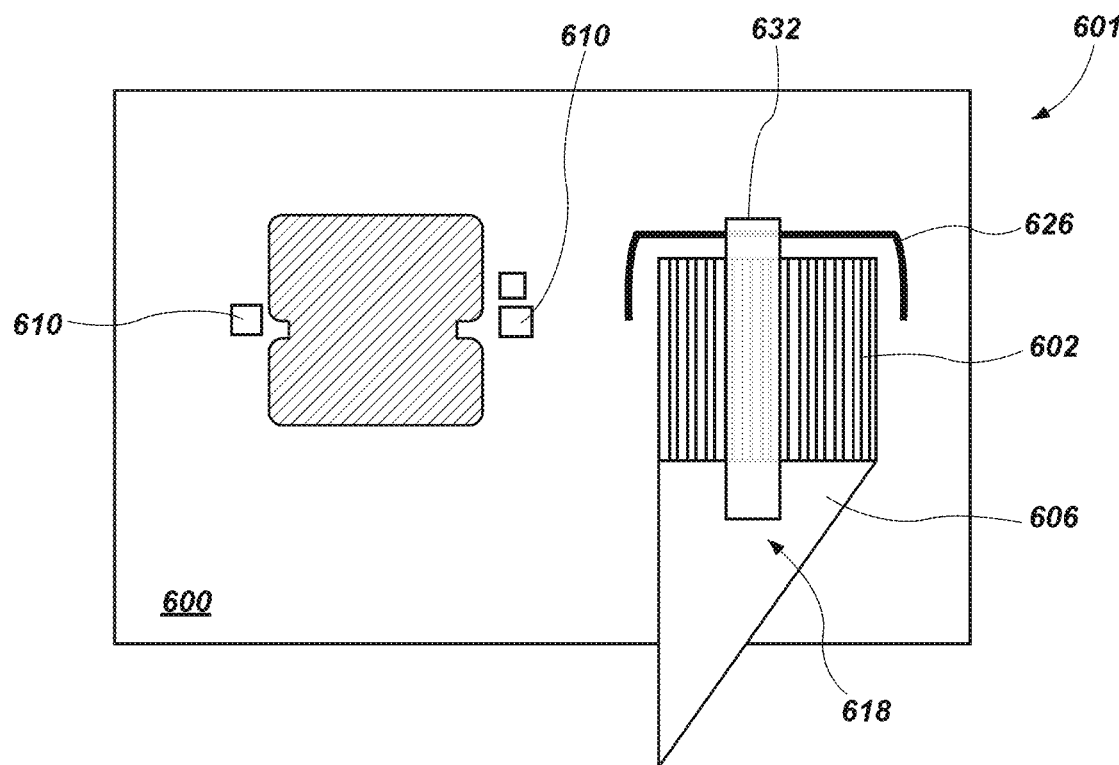

Referring to FIGS. 6D and 6E together, upon securing the initial deep lamella 618 to the probe tip 230 of the probe 228, the process 201 may include lowering the probe 228 until the initial deep lamella 618 is placed on the upper surface 604 of the wafer 600 proximate to the nest 626 on the upper surface 604 of the wafer 600. For instance, the initial deep lamella 618 may be laid flat on the upper surface 604 of the wafer 600. As noted above, in some embodiments, the nest 626 may assist in breaking an electrostatic connection between the probe 228 and the initial deep lamella 618.

In one or more embodiments, the process 601 may include placing the initial deep lamella 618 on the upper surface 604 of the wafer 600 at a location proximate to the nest 626 and then sliding the initial deep lamella 618 along the upper surface 604 of the wafer 600 into the nest 626. For instance, the process may include utilizing the probe 228 to slide the initial deep lamella 618 up against the nest 626 until the nest 626 at least substantially surrounds at least a portion of an outer periphery of the upper portion 602 of the initial deep lamella 618. For instance, the process 601 may include aligning the initial deep lamella 618 within the nest 626. In other embodiments, the probe 228 may place the initial deep lamella 618 directly into the nest 626 such that the nest 626 at least substantially surrounds an outer periphery of the upper portion 602 of the initial deep lamella 618.

In some embodiments, disposing the initial deep lamella 618 directly into the nest 626 and/or sliding the initial deep lamella 618 may result in the initial deep lamella 618 not being aligned within the nest 226. For instance, the initial deep lamella 618 may be askew within the nest 626 and/or the focusing ion beam 118 (which is used to mill additional lamella (described below)) of the dual beam system 110. Accordingly, in one or more embodiments, the process may include adjusting and/or reorienting the initial deep lamella 618 with the probe 228 to properly align the initial deep lamella 618 and to ensure that the features of interest included within the upper portion 602 of the initial deep lamella 618 are included within a planar second wide, shallow, and thin lamella (described below) (referred to hereinafter as a "planar shallow lamella". In some instances, the initial deep lamella 618 may be adjusted and/or reoriented automatically by one or more of the lamella extraction station and the dual beam system 110. For instance, the position of the initial deep lamella 618 may be adjusted to align the tall internal structures (i.e., the tall features of interest) within the upper portion 602 of the initial lamella with the focused ion beam 118 of the dual beam system 110. As is described in greater detail below in regard to FIGS. 8A-8D, in one or more embodiments, a relatively large window (e.g., milled out portion, a thinned portion, etc.) may be formed in the initial deep lamella 618 to expose the tall internal structures 646 (e.g., crystalline structures) of the initial deep lamella 618, and the tall internal structures 646 may be utilized to align the initial deep lamella 618. In additional embodiments, the initial deep lamella 618 may be aligned via any of the manners described above in regard to FIGS. 2H, 2I, and 4A-4E.

Referring to FIGS. 6B-6D together, in one or more embodiments, as noted above, the initial deep lamella 618, which is milled from the wafer 600, may include the upper portion 602 and a bulk silicon base portion 606. Furthermore, the upper portion 602 may be at a top of the initial deep lamella 618. As also noted above the upper portion 602 may include the tall features (e.g., tall internal structures 646, crystalline structures, etc.) of interest, and STEM images of those tall features may be desirable to determine a quality of the wafer 600, defects in the wafer 600, etc. Furthermore, as shown in FIG. 6E, in some embodiments, the upper portion 602 of the initial deep lamella 618 may be disposed against or proximate to the nest 626. Moreover, as will be discussed in greater detail below, the upper portion 602 of the initial deep lamella 618 may be a targeted portion in creating a second lamella (i.e., the planar shallow lamella).

In embodiments where the wafer 600 is unloaded from the dual beam system 110, after placing the initial deep lamella 618 within the nest 626, the process 601 may include reloading the wafer 600 into the dual beam system 110. Furthermore, in reference to FIG. 6F, the process 601 may include depositing a material 632 to adhere the initial deep lamella 618 to the upper surface 604 of the wafer 600 and at least substantially hold the initial deep lamella 618 in place. In some embodiments, the material 632 may include tungsten, carbon, and/or TEOS. In one or more embodiments, the material 632 may be deposited utilizing the gas delivery system 146 of the dual beam system 110. In one or more embodiments, the material 632 may be disposed in an elongated shape (e.g., an elongated rectangle) having a longitudinal axis at least substantially parallel to longitudinal axes of the features of interest within the initial deep lamella 618. For instance, the longitudinal axis of the elongated shape of material 632 may be at least substantially perpendicular to an original top surface of the upper portion 602 of the initial deep lamella.

Additionally, the process 601 may include depositing one or more fiducial markers 634 proximate to and/or on the initial deep lamella 618 and identifying an additional milling site on the wafer 600. As is known in the art, the fiducial markers 634 may be utilized by the dual beam system 110 for future processing (e.g., milling of a second lamella). For instance, the fiducial markers 634 may assist the dual beam system 110 in orienting and moving (e.g., scanning) the focused ion beam 118. The fiducial markers 634 may be deposited via the gas delivery system 146 of the dual beam system 110. In some embodiments, an operator of the dual beam system 110 may input parameters of an overall additional milling procedure (e.g., an additional recipe) via the user interface described above to cause the dual beam system 110 to deposit the material 632 and/or the fiducial markers 634 according to the input parameters of the additional milling procedure.

In one or more embodiments, the one or more fiducial markers 634 may be deposited proximate longitudinal ends of the elongated shape of material 632. As a result, a first fiducial marker 634 may be deposited on the upper surface 604 of the wafer 600 on a side of the nest 626 opposite the initial deep lamella 618. Additionally, a second fiducial marker 634 may be deposited on a lateral side surface of a portion of the initial deep lamella 618 (e.g., on the bulk silicon base portion 606 of the initial deep lamella 618). Accordingly, a line extending between the first and second fiducial markers 234 may be at least substantially parallel to the features of interest within the initial deep lamella 618 and perpendicular to a top surface 603 of the upper portion 602 of the initial deep lamella 618.

Figure 6G:
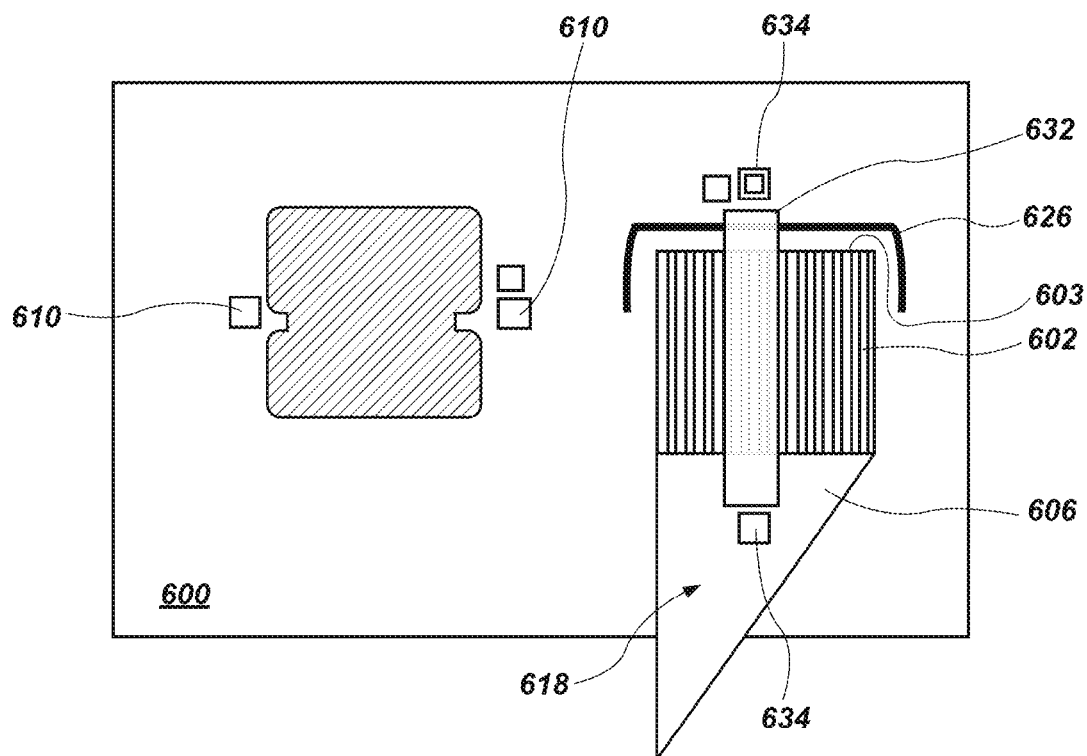

After the fiducial markers 634 have been deposited, with reference to FIG. 6G, the process 601 may include milling a second lamella (referred to hereinafter as the "planar shallow lamella 638") to include at least a portion of the upper portion 602 of the initial deep lamella 618 and at least a portion of the bulk silicon base portion 606 of the initial deep lamella 618. Moreover, the process 601 may include milling the planar shallow lamella 638 to include at least substantially an entire length of at least one tall internal structure 646 of the initial deep lamella 618. For instance, the planar shallow lamella 638 may be milled such that a width (i.e., a lateral width) of the planar shallow lamella 638 extends along an original longitudinal length (e.g., an original depth) of the initial deep lamella 618 disposed on the upper surface 604 of the wafer 600. Furthermore, the planar shallow lamella 638 may be milled via any of the manners described above in regard to FIGS. 2A-2D and 2K. In some embodiments, an operator of the dual beam system 110 may input parameters of the overall additional milling procedure (e.g., an additional recipe) via the user interface described above to cause the dual beam system 110 to mill the planar shallow lamella 638 according to the input parameters of the additional milling procedure.

Figure 6H:
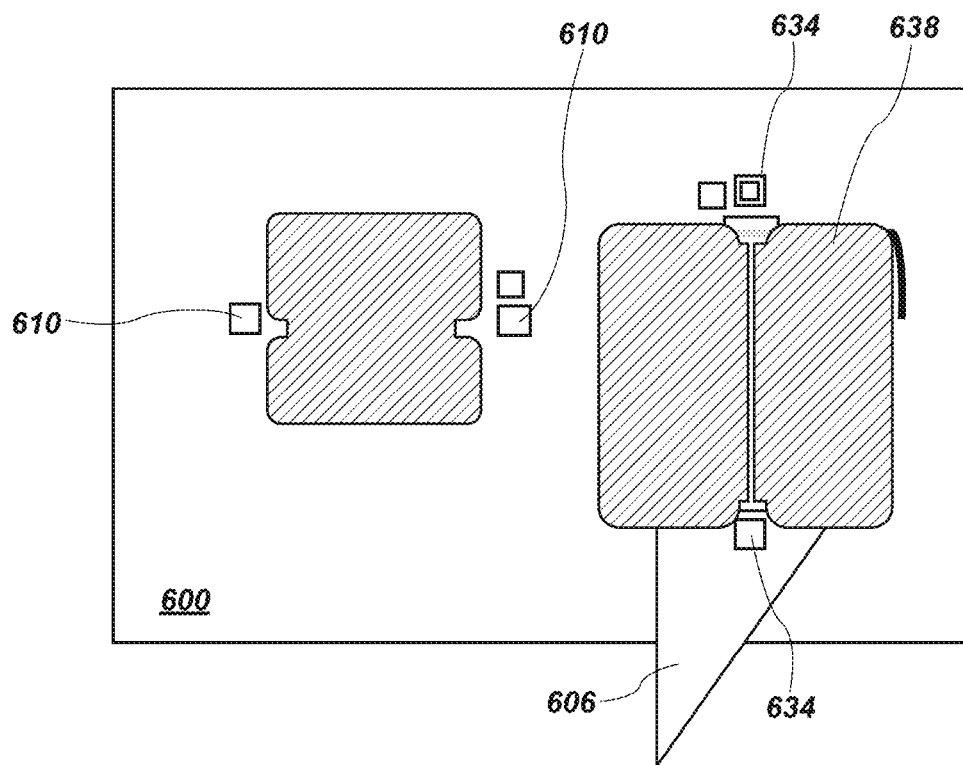

Referring to FIG. 6H, in some embodiments, milling the planar shallow lamella 638 may further include thinning the planar shallow lamella 638 with the focused ion beam 118. For instance, the dual beam system 110 may thin the planar shallow lamella 638 utilizing the focused ion beam 118. As a non-limiting example, the planar shallow lamella 638 may be thinned via any of the manners known in the art. Furthermore, milling the planar shallow lamella 638 may, optionally, include any cleaning processes known in the art.

In some embodiments, an operator of the dual beam system 110 may input parameters of the overall additional milling procedure (e.g., an additional recipe) via the user interface described above to cause the dual beam system 110 to thin the planar shallow lamella 638 according to the input parameters of the additional milling procedure.

Figure 6I:
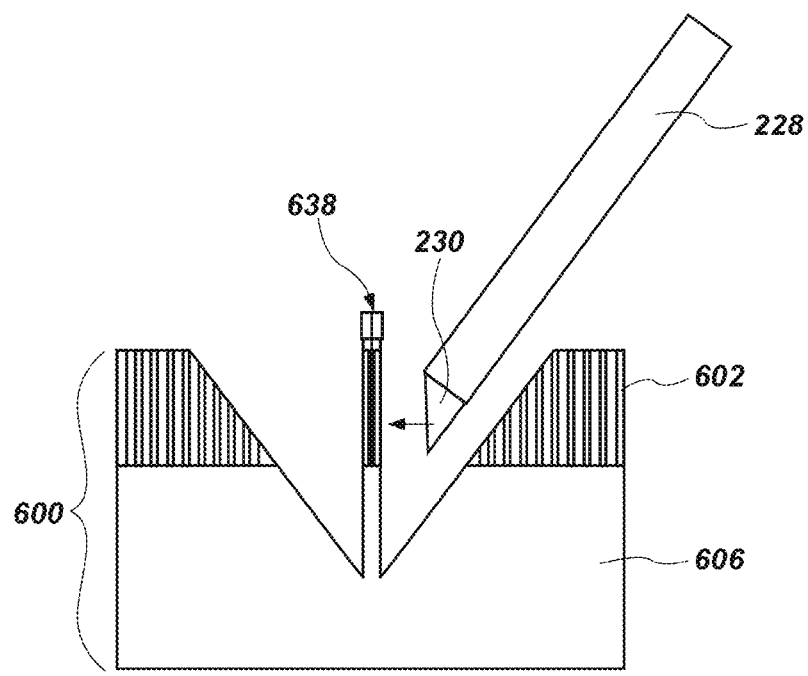
Figure 6J:
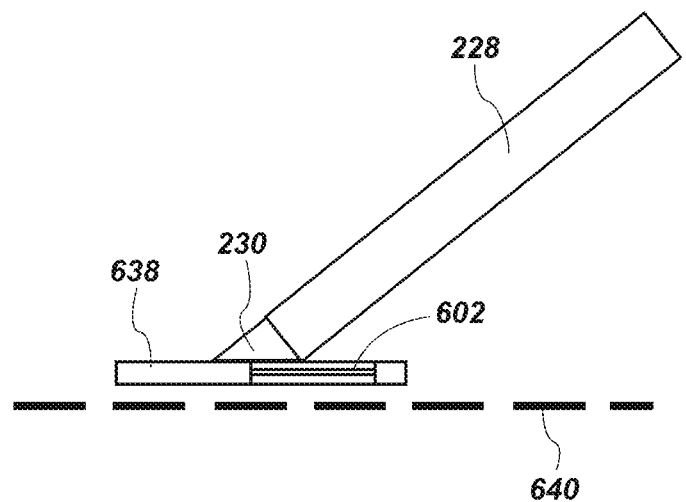

In reference to FIGS. 6I and 6J, after milling the planar shallow lamella 638, the process 601 may include lifting the planar shallow lamella 638 from the second milling site and placing the planar shallow lamella 638 on an amorphous carbon grid 640 for imaging with a TEM and/or STEM. For example, the process 601 may include lifting the planar shallow lamella 638 via any of the methods described above in regard to FIGS. 2F and 6B. Furthermore, the process 601 may include placing the planar shallow lamella 638 on the amorphous carbon grid 640 via any of the methods described above in regard to FIGS. 2H and 6D. As will be understood in the art, the amorphous carbon grid 640 may assist in breaking any electrostatic connection between the probe 228 and the planar shallow lamella 638.

After placing the planar shallow lamella 638 on the amorphous carbon grid 640, the process 601 may include imaging and performing metrology on the planar shallow lamella 638 via TEM and/or STEM systems. For instance, the process 601 may include performing automated imaging and metrology utilizing a Thermo Scientific Metrios™ system. Although specific TEM and STEM imaging/metrology systems are described herein, the disclosure is not so limited, and the process 601 may include imaging and/or performing metrology analysis via any TEM and/or STEM system known in the art.

Figure 7:
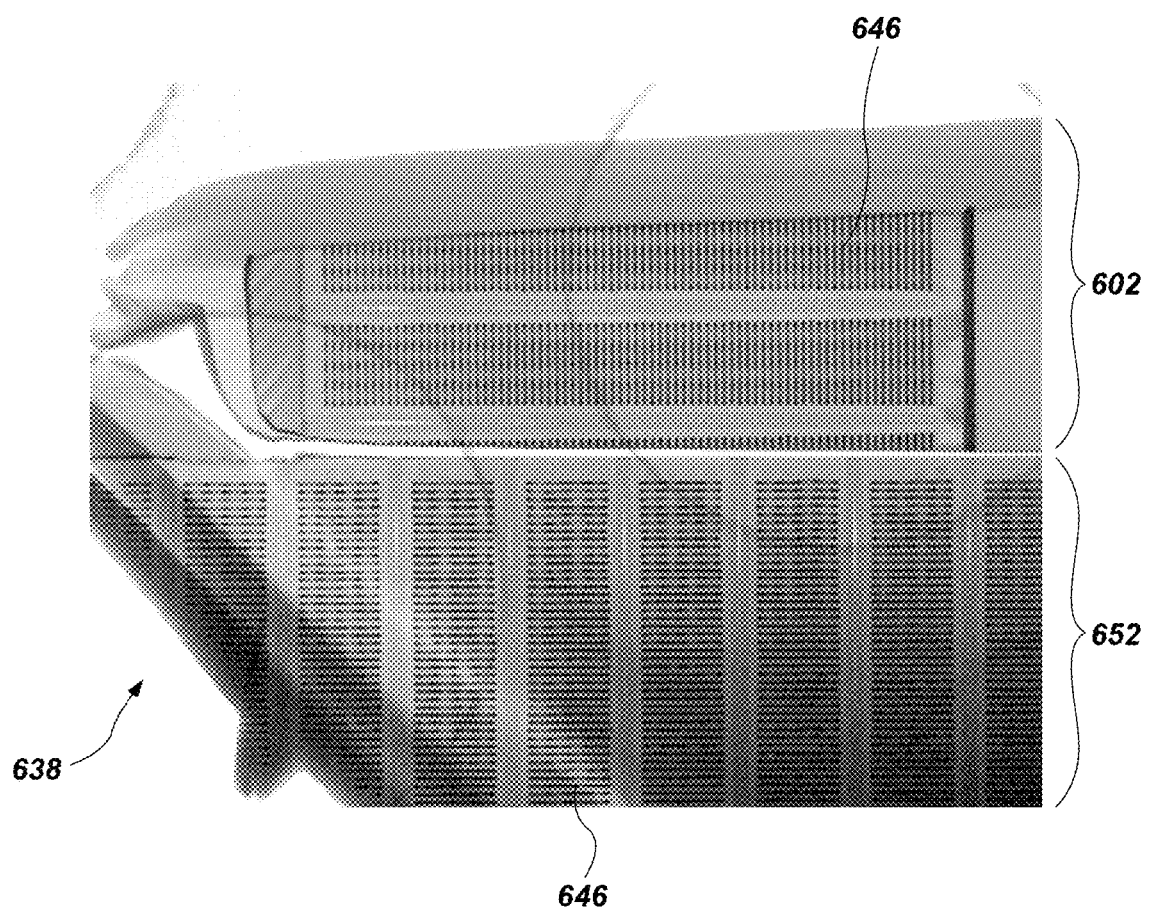
FIG. 7 is an image of a sample of a semiconductor device according to one or more embodiments of the present disclosure.

FIG. 7 shows an example image obtained via STEM imaging that includes the upper portion 602 of the initial deep lamella 618 along with a respective upper portion 652 of the planar shallow lamella 638. As shown, because the initial deep lamella 618 was milled, placed on its side on the upper surface 604 of the wafer 600, milled again as a portion of the planar shallow lamella 638, and then placed on the amorphous grid, when the planar shallow lamella 638 and, specifically, the portion of the planar shallow lamella 638 including the upper portion 602 of the initial deep lamella 618 is imaged, a planar cross-section view of the initial deep lamella 618 is achieved that is not achievable utilizing conventional operations of the dual beam system 110. For instance, the planar shallow lamella 638 includes a first cross-sectional view of the tall internal structures 646 of the wafer 600 within the portion of the planar shallow lamella 638 not comprised of the initial deep lamella 618, and a second cross-sectional view of the tall internal structures 646 that is orthogonal to the first cross-sectional view within the portion of the planar shallow lamella 638 comprising the initial deep lamella 618. The first cross-sectional view may include a view depicting the tall internal structures 646 as if viewed from a plane orthogonal to the upper surface 604 of the wafer 600, and the second cross-sectional view may include a view depicting the tall internal structures 646 as if viewed from a plane parallel to the upper surface 604 of the wafer 600.

Moreover, the process 601 provides a method for creating TEM/STEM lamella of high-aspect ratio samples and having relatively tall internal structures 646 which are typically outside of a usable range of a conventional dual beam system. Furthermore, because the process 601 described herein provides both the first cross-sectional view and the second cross-sectional view, the process 201 may provide more complete images of the tall internal structures 646 of the wafer 600 in comparison to conventional methods only include the first cross-sectional view. As a result, the process 601 may provide more complete information regarding the tall internal structures 646 of the wafer 600. Accordingly, a more complete analysis can be achieved utilizing the process 601 described herein in comparison to conventional processes. Due to the more complete analysis, a quality of the wafer 600 and devices formed thereon may be better determined, which results in better products and more flaws detected.

FIGS. 8A-8D represent an additional process 801 that can be utilized in conjunction with the process 601 described above to align the initial deep lamella 618 on the upper surface 604 of the wafer 600 and for subsequent milling. In some embodiments, the process 801 can take place after depositing the material 632 over the initial deep lamella 618. Referring to FIGS. 8A-8D together, which show the initial deep lamella 618 disposed within the nest 626, in some embodiments, the process 801 may include milling a window 844 within the initial deep lamella 618. The window 844 may include any of the windows described above in regard to FIGS. 4A-4E. Furthermore, the window 844 may be milled utilizing the focused ion beam 118 of the dual beam system 110 via any of the methods described above in regard to FIGS. 1-2N and 4A-4E. In some instances, the milling the window 844 may include milling the window 844 at least partially within (e.g., to include at least a portion of) the upper portion 602 of the initial deep lamella 618. Milling the window 844 within the upper portion 602 of the initial deep lamella 618 may expose the tall internal structures 646 (e.g., features of interest) of the initial deep lamella 618. As will be appreciated by one of ordinary skill in the art, in some embodiments, the tall internal structures 646 may be oriented relative to one another in at least substantially parallel lines.

In some embodiments, the window 844 may span at least a majority of a width of the upper portion 602 of the initial deep lamella 618. For example, the window 844 may extend longitudinally in a direction perpendicular to a direction in which the tall internal structure 646 extend within the initial deep lamella 618. Furthermore, the window 844 may extend over multiple tall internal structures 646.

Figure 8A:
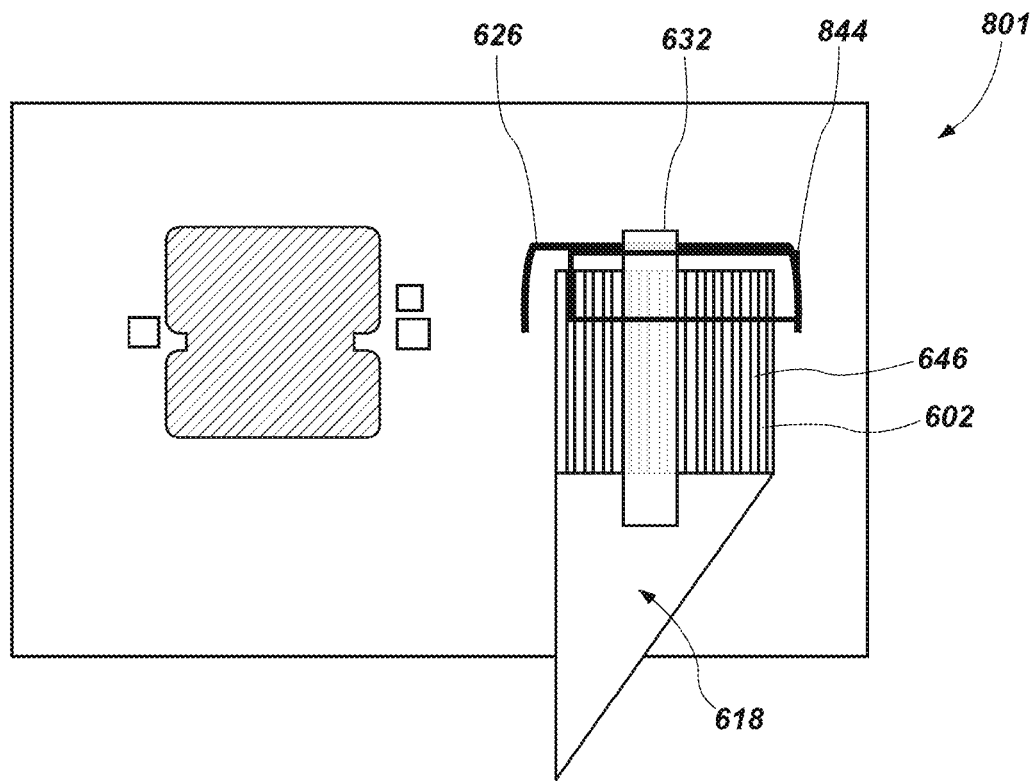
FIGS. 8A-8D illustrate another process for preparing a sample of a semiconductor device for TEM and/or STEM imaging according to one or more embodiments of the present disclosure.
Figure 8B:
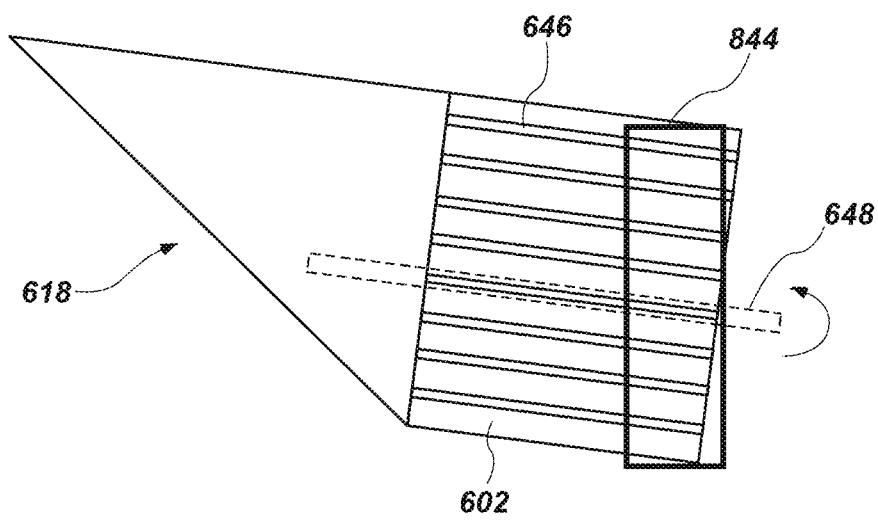
Figure 8C:
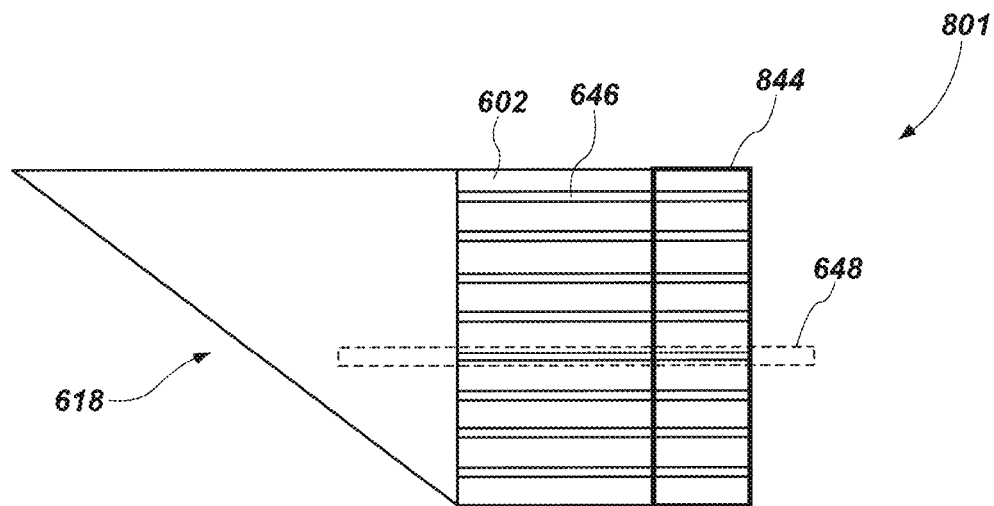

Accordingly, once the window 844 in milled within the initial deep lamella 618, the process 801 may include determining if the tall internal structures 646 are oriented as desired relative to the wafer 600, the nest 626, and/or a desired planar shallow lamella 638 thickness and placement (referred to as "648" within FIGS. 8B and 8C). In some embodiments, the tall internal structures 646 of the initial deep lamella 618 may need to be aligned with the focusing ion beam 118 to achieve an optimal image of the later-to-be-formed planar shallow lamella 638. In other words, the tall internal structures 646 and/or the orientation of the tall internal structures 646 need to form a zero-degree angle with a direction in which the focusing ion beam 118 translates (e.g., moves). In some embodiments, the dual beam system 110 may utilize pattern recognition and edge finding software to determine the positions and orientations of the tall internal structures 646, and as a result, the position and orientation of the overall initial deep lamella 618 on the upper surface 604 of the wafer 600. For instance, the dual beam system 110 may utilize pattern recognition and edge finding software to determine the position of the tall internal structures 646 and as a result, the initial deep lamella 618, in each of the three axes (X, Y, and Z). Additionally, based on the determined locations and orientations of the tall internal structures 646 and initial deep lamella 618, the dual beam system 110 determines an amount of rotation needed in each of the three axes to properly align the initial deep lamella 618 with the focused ion beam 118 of the dual beam system 110. Furthermore, based on the determined amount of rotation, the dual beam system 110 and/or operator may utilize the micromanipulator 147 to rotate the initial deep lamella 618 to achieve proper alignment with the focused ion beam 118 of the dual beam system 110. In other embodiments, the initial deep lamella 618 may be left as is, and the focusing ion beam 118 can be rotated instead to align the focusing ion beam 118 with the tall internal structures 646.

In some embodiments, the relatively large size of the window 844 (e.g., the large size of the window 844 relative to the window 244 described above in regard to FIGS. 4A-4E) may enable dual beam system 110 to more accurately determine a position and location of the initial deep lamella 618 and, as a result, achieve a finer and more accurate rotation of the initial deep lamella 618. In particular, because of the relatively large size of the window 844, the window 844 may expose more tall internal structures 646 in comparison to the window 244 described above in regard to FIGS. 4A-4E. Furthermore, because the tall internal structures 646 of the initial deep lamella 618 have a greater length than the internal structures 246 of the initial lamella 218, a more accurate alignment may be necessary to ensure that a second lamella (i.e., the planar shallow lamella 638) is properly centered about a tall internal structure 646 of the initial deep lamella 618. For instance, because the tall internal structures 646 of the initial deep lamella 618 are relatively long, any error in alignment would be magnified at longitudinal ends of the tall internal structures 646 and may result in the planar shallow lamella 638 not being properly aligned. However, because the window 844 may expose more tall internal structures 646 in comparison to the window 244, the dual beam system 110 may have more data (i.e., patterns and edges) to determine a position and location of the initial deep lamella 618 and any required rotations of the initial deep lamella 618.

Figure 8D:
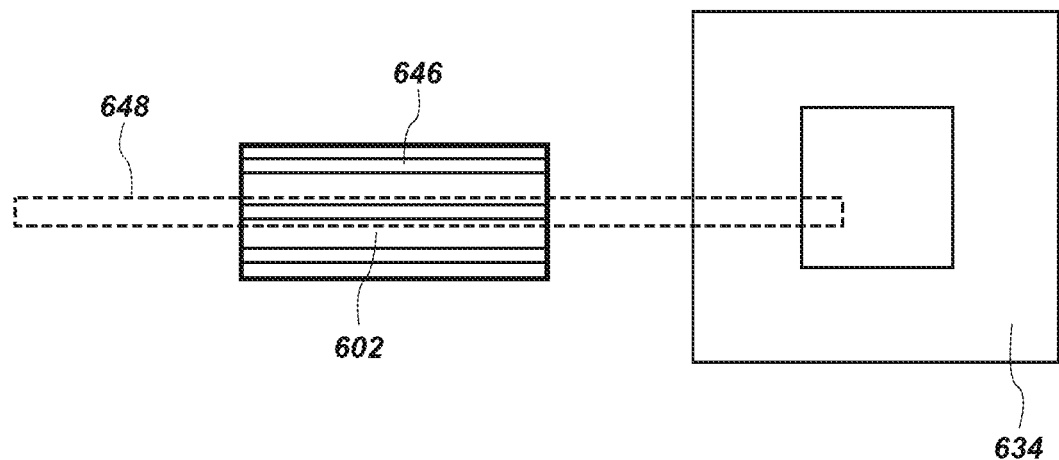

Referring to FIGS. 8C and 8D together, once the initial deep lamella 618 is properly oriented, the process 401 may include depositing one or more fiducial markers 634 relative to the initial deep lamella 618 via any of the methods described above in regard to FIGS. 2A and 6F. In some embodiments, placement of the fiducial markers 634 may be determined based on location of the tall internal structures 646 within the Y-axis, determined above in regard to FIGS. 8A and 8B. Moreover, the fiducial markers 634 may be deposited, and an offset between a center of the fiducial marker 634 and a center longitudinal axis of an internal structure 646 about which the planar shallow lamella 638 may be milled is measured. Furthermore, the process 801 may include milling the planar shallow lamella 638 via any of the methods described above in regard to FIGS. 2K and 6G. Moreover, the process 801 may include thinning the planar shallow lamella 638 via any of the methods described above in regard to FIG. 2L. In additional embodiments, one or more additional windows may be formed in the planar shallow lamella 638 via any of the manners described above in regard to FIG. 4E.

Figure 9:
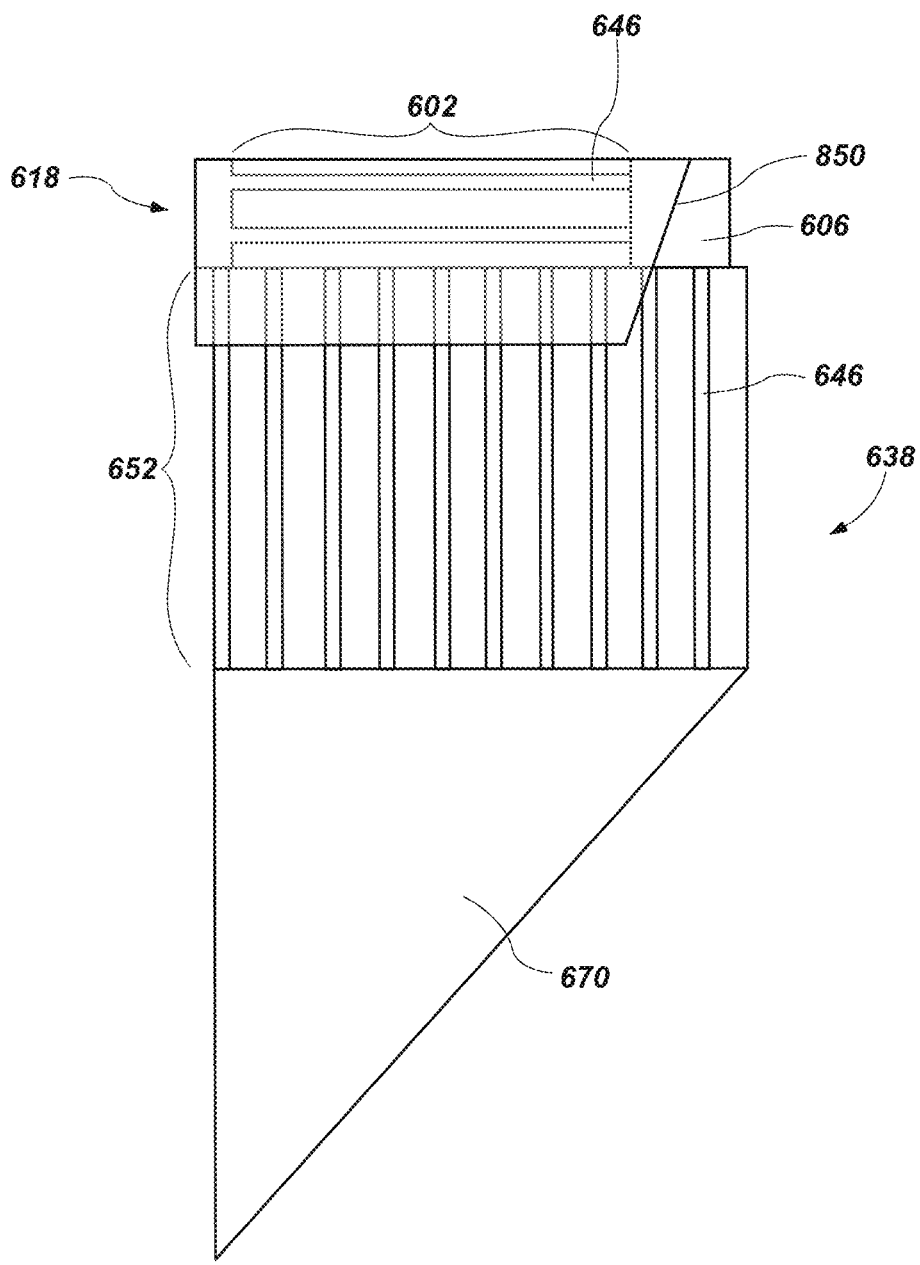
FIG. 9 shows a front view of a planar shallow lamella prepared via one or more of the processes described herein.

FIG. 9 shows a front view of a planar shallow lamella 638 formed via process 601 and process 801. As shown, the planar shallow lamella 638 may include the upper portion 602 of the initial deep lamella 618 providing a planar view of the features of interest (e.g., tall internal structures 646) of the wafer 600. The planar shallow lamella 638 may further include a window 850 formed in the upper portion 602 (i.e., formed via any of the manners described above in regard to FIG. 4E) and the bulk silicon base portion 606 of the initial deep lamella 618. The planar shallow lamella 638 may also include a respective upper portion 652 below the initial deep lamella 618 including features of interest of the wafer 600 that can be viewed from an angle orthogonal to the planar view of the initial deep lamella 618. As shown in FIG. 9, the window 850 may extend into the upper portion 652 of the planar shallow lamella 638. Additionally, the planar shallow lamella 638 may include a respective bulk silicon base portion 670.

Some embodiments of the present disclosure include a method of preparing a sample. The method may include loading a wafer on a stage, milling an initial lamella within the wafer using a focused ion beam, lifting the initial lamella out of the wafer, placing the initial lamella on an upper surface of the wafer on a lateral side of the initial lamella, milling a planar lamella out of a portion of the initial lamella and the wafer beneath the initial lamella, lifting the planar lamella out of the wafer, and placing the planar lamella on a carbon grid.

One or more embodiments of the present disclosure include method of preparing a sample. The method may include loading a wafer on a support surface, milling an initial lamella within the wafer using a focused ion beam, lifting the initial lamella out of the wafer, placing the initial lamella on an upper surface of the wafer on a lateral side of the initial lamella, milling a window within an upper portion of the initial lamella exposing internal structures of the initial lamella, based at least partially on the exposed internal structures of the initial lamella, aligning the initial lamella on the upper surface of the wafer, milling a planar lamella out of a portion of the initial lamella and the wafer beneath the initial lamella, lifting the planar lamella out of the wafer, and placing the planar lamella on a carbon grid.

Some embodiments of the present disclosure include a method of preparing a sample. The method may include placing a wafer on a support, milling an initial lamella within the wafer using a focused ion beam, lifting the initial lamella out of the wafer, placing the initial lamella on an upper surface of the wafer on a lateral side of the initial lamella, milling a planar lamella out of a portion of the initial lamella and the wafer beneath the initial lamella, milling a window within a bulk silicon portion of the portion of the initial lamella included within the planar lamella, lifting the planar lamella out of the wafer, placing the planar lamella on a carbon grid and based at least partially on a configuration of the window formed in the bulk silicon portion of the portion of the initial lamella included within the planar lamella, aligning the planar lamella with an electron beam of a TEM imaging system or a STEM imaging system.

One or more embodiments of the present disclosure include a method of preparing a sample. The method may include milling an initial lamella within a wafer, lifting the initial lamella out of the wafer, placing the initial lamella flat on an upper surface of the wafer, and milling a planar lamella to include at least a portion of the initial lamella.

Some embodiments of the present disclosure include a method of preparing a sample. The method may include disposing a wafer on a surface, milling an initial lamella within the wafer using a focused ion beam, lifting the initial lamella out of the wafer, placing the initial lamella on an upper surface of the wafer on a lateral side of the initial lamella, milling a window within an upper portion of the initial lamella to expose internal structures of the initial lamella, based at least partially on the exposed internal structures of the initial lamella, aligning the initial lamella on the upper surface of the wafer, milling a planar lamella out of a portion of the initial lamella and the wafer beneath the initial lamella, milling an additional window within a bulk silicon portion of the portion of the initial lamella included within the planar lamella, lifting the planar lamella out of the wafer, placing the planar lamella on a carbon grid, and based at least partially on a configuration of the additional window formed in the bulk silicon portion of the portion of the initial lamella included within the planar lamella, aligning the planar lamella with an electron beam of a TEM imaging system or a STEM imaging system.

One or more embodiments of the present disclosure include a method of preparing a sample. The method may include milling an initial lamella within a wafer using a focused ion beam, the initial lamella comprising a upper portion and a lower portion, the upper portion comprising a portion of the initial lamella initially proximate to an upper surface of the wafer, lifting the initial lamella out of the wafer with a lamella extraction station, placing the initial lamella flat on an upper surface of the wafer with the lamella extraction station, milling a planar lamella to include at least a portion of the upper portion of the initial lamella, and imaging the planar lamella via a TEM or STEM imaging system to include imaging of the at least a portion of the upper portion of the initial lamella.

Some embodiments of the present disclosure include a method of preparing a sample. The method may include milling an initial deep lamella within a wafer using a focused ion beam, the initial deep lamella comprising at least one internal structure within an upper portion of the initial deep lamella, lifting the initial deep lamella out of the wafer, placing the initial deep lamella on an upper surface of the wafer on a lateral side of the initial lamella, milling a planar shallow lamella out of a portion of the initial deep lamella and the wafer beneath the initial deep lamella to include at least substantially an entire length of the at least one internal structure of the initial deep lamella, lifting the planar shallow lamella out of the wafer; and placing the planar shallow lamella on a carbon grid.

One or more embodiments of the present disclosure include a method of preparing a sample. The method may include milling an initial deep lamella within a wafer using a focused ion beam, the initial deep lamella comprising internal structures within an upper portion of the initial deep lamella, lifting the initial deep lamella out of the wafer, placing the initial deep lamella on an upper surface of the wafer on a lateral side of the initial lamella, milling a window within an upper portion of the initial deep lamella exposing multiple internal structures of the initial deep lamella, based at least partially on the exposed multiple internal structures of the initial deep lamella, aligning the initial deep lamella on the upper surface of the wafer, milling a planar shallow lamella out of a portion of the initial deep lamella and the wafer beneath the initial lamella to include at least substantially an entire length of at least one internal structure of the internal structures of the initial deep lamella, lifting the planar shallow lamella out of the wafer, and placing the planar shallow lamella on a carbon grid.

Some embodiments of the present disclosure include a method of preparing a sample. The method may include milling an initial deep lamella within a wafer, lifting the initial deep lamella out of the wafer, placing the initial deep lamella flat on an upper surface of the wafer, depositing an elongated shape of material over the initial deep lamella, the elongated shape having a longitudinal length being at least substantially perpendicular to a top surface of the initial deep lamella, and milling a planar lamella to include at least a portion of the initial lamella.

The embodiments of the disclosure described above and illustrated in the accompanying drawings do not limit the scope of the disclosure, which is encompassed by the scope of the appended claims and their legal equivalents. Any equivalent embodiments are within the scope of this disclosure. Indeed, various modifications of the disclosure, in addition to those shown and described herein, such as alternate useful combinations of the elements described, will become apparent to those skilled in the art from the description. Such modifications and embodiments also fall within the scope of the appended claims and equivalents.

What is claimed is:

1. A method of preparing a sample, the method comprising:
   placing a first lamella on an upper surface of a wafer; and
   milling a second lamella to include at least a portion of the first lamella.

2. The method of claim 1, further comprising milling the first lamella within the wafer using a focused ion beam.

3. The method of claim 1, wherein placing a first lamella on a upper surface of a wafer comprises placing the first lamella on the upper surface of the wafer on a lateral side of the first lamella.

4. The method of claim 1, wherein milling a second lamella to include at least a portion of the first lamella comprises milling the second lamella out of a portion of the first lamella and the wafer beneath the first lamella.

5. The method of claim 1, further comprising:
   lifting the second lamella out of the wafer; and
   placing the second lamella on a carbon grid.

6. The method of claim 1, further comprising:
   forming a nest on the upper surface of the wafer proximate to a milling site of the first lamella; and
   placing the first lamella within the nest on the upper surface of the wafer.

7. The method of claim 6, wherein the nest comprises at least one of carbon, tungsten, or tetraethyl orthosilicate.

8. The method of claim 1, wherein milling a second lamella to include at least a portion of the first lamella comprises milling the second lamella to include an upper portion of the first lamella.

9. The method of claim 1, further comprising imaging the second lamella on a carbon grid via a TEM or STEM imaging system to include imaging of the portion of the first lamella.

10. A method for preparing a sample, the method comprising:
    placing a wafer on a movable stage of a dual beam system;
    milling an initial lamella within the wafer using a focused ion beam of the dual beam system;
    lifting the initial lamella with a micromanipulator of the dual beam system;
    placing the initial lamella on an upper surface of the wafer with the micromanipulator; and
    milling a planar lamella to include at least a portion of the initial lamella with the focused ion beam of the dual beam system.

11. The method claim 10, depositing a material over the initial lamella on the upper surface of the wafer with a gas delivery system of the dual beam system to secure the wafer prior to milling the planar lamella.

12. The method of claim 10, further comprising depositing one or more fiducial markers around the initial lamella on the upper surface of the wafer with a gas delivery system to identify a milling site of the planar lamella and prior to milling the planar lamella.

13. The method of claim 10, further comprising:
forming a nest on the upper surface of the wafer proximate to a milling site of the initial lamella with a gas delivery system of the dual beam system;
placing the initial lamella within the nest on the upper surface of the wafer with the micromanipulator; and
based at least partially on exposed internal structures of the initial lamella, aligning the initial lamella within the nest with a probe of the dual beam system.

14. The method of claim 10, further comprising:
lifting the planar lamella out of the wafer with the micromanipulator; and
placing the planar lamella on a carbon grid with the micromanipulator.

15. The method of claim 10, wherein milling a planar lamella out of a portion of the initial lamella comprises thinning the planar lamella and cleaning the planar lamella with the focused ion beam.

16. A method of preparing a sample, the method comprising:
placing a first lamella on an upper surface of a wafer;
milling a window in an upper portion of the first lamella to expose at least one internal structure of the first lamella;
based at least partially on the exposed at least one internal structure of the first lamella, aligning the first lamella on the upper surface of the wafer; and
milling a second lamella out of a portion of the first lamella and the wafer to include at least substantially an entire length of the at least one internal structure of the first lamella.

17. The method of claim 16, further comprising:
forming a nest on the upper surface of the wafer proximate to a milling site of the first lamella;
placing the first lamella within the nest on the upper surface of the wafer; and
based at least partially on the exposed at least one internal structure of the first lamella, aligning the first lamella within the nest.

18. The method of claim 16, further comprising depositing at least one first fiducial marker on the upper surface of the wafer proximate the first lamella and at least one second fiducial marker on a lateral side surface of the first lamella to identify a milling site of the second lamella and prior to milling the second lamella.

19. The method of claim 16, further comprising depositing a material over the first lamella on the upper surface of the wafer to secure the first lamella prior to milling the second lamella.

20. The method of claim 19, wherein depositing a material over the first lamella comprises depositing a material as an elongated shape having a longitudinal length being at least substantially parallel to a longitudinal length of the at least one internal structure of the first lamella.

* * * * *

UNITED STATES PATENT AND TRADEMARK OFFICE
CERTIFICATE OF CORRECTION

PATENT NO. : 10,539,489 B2  
APPLICATION NO. : 16/526704  
DATED : January 21, 2020  
INVENTOR(S) : Jamie C. Porter et al.

Page 1 of 1

It is certified that error appears in the above-identified patent and that said Letters Patent is hereby corrected as shown below:

In the Specification
Column 16, Line 41, change "(e.g., a and 0 tilts)" to --(e.g., α and β tilts)--
Column 21, Line 7, change "FIGS. 6I and 6J" to --FIGS. 6I and 6J--

Signed and Sealed this
Fifth Day of May, 2020

Andrei Iancu
*Director of the United States Patent and Trademark Office*